(12) United States Patent
Perry et al.

(10) Patent No.: US 8,551,096 B2
(45) Date of Patent: *Oct. 8, 2013

(54) DIRECTIONAL DELIVERY OF ENERGY AND BIOACTIVES

(75) Inventors: Mike Perry, Los Altos, CA (US); Brian D. Conn, San Diego, CA (US); Rolfe T. Gustus, San Diego, CA (US); Ronda Schreiber, Poway, CA (US); Corbett Stone, San Diego, CA (US); Michael F. Hoey, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 567 days.

This patent is subject to a terminal disclaimer.

(21) Appl. No.: 12/778,037

(22) Filed: May 11, 2010

(65) Prior Publication Data
US 2011/0130708 A1    Jun. 2, 2011

Related U.S. Application Data

(60) Provisional application No. 61/177,744, filed on May 13, 2009.

(51) Int. Cl.
*A61B 17/56* (2006.01)

(52) U.S. Cl.
USPC ........... 606/76; 604/96.01; 604/382; 606/907

(58) Field of Classification Search
CPC ..................................... A61B 17/56
USPC ................ 424/1.29, 417, 490; 604/21, 96.01, 604/103.08, 265, 382, 500; 606/27, 76, 606/192, 907
See application file for complete search history.

(56) References Cited

U.S. PATENT DOCUMENTS

| | | | |
|---|---|---|---|
| 1,167,014 A | 1/1914 | O'Brien |
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |

(Continued)

FOREIGN PATENT DOCUMENTS

| | | |
|---|---|---|
| CA | 2384866 A1 | 5/2001 |
| CN | 101583323 A | 11/2009 |

(Continued)

OTHER PUBLICATIONS

Scheller et al., "Potential Solutions to the Current Problem: Coated Balloon," EuroIntervention, Aug. 2008; 4 Suppl C: C63-66.

(Continued)

*Primary Examiner* — Nicholas Lucchesi
*Assistant Examiner* — Gerald Landry, II
(74) *Attorney, Agent, or Firm* — Seager, Tufte & Wickhem, LLC

(57) ABSTRACT

Systems and methods are disclosed for the treatment of a target tissue by directionally delivering energy and/or bioactive materials to achieve a therapeutic effect. A balloon catheter system having a balloon portion and a plurality of electrodes may be energized to selectively deliver energy, bioactive materials, or a combination thereof to target tissue including tissues disposed about a lumen. The tissue may be targeted by applying energy, making tissue impedance analysis, and further selectively energizing electrodes through the use of an energy source with a controller.

25 Claims, 13 Drawing Sheets

(56) References Cited

U.S. PATENT DOCUMENTS

| | | |
|---|---|---|
| 3,540,431 A | 11/1970 | Mobin-Uddin |
| 3,952,747 A | 4/1976 | Kimmell, Jr. |
| 3,996,938 A | 12/1976 | Clark, III |
| 4,046,150 A | 9/1977 | Schwartz et al. |
| 4,290,427 A | 9/1981 | Chin |
| 4,587,975 A | 5/1986 | Salo et al. |
| 4,682,596 A | 7/1987 | Bales et al. |
| 4,709,698 A | 12/1987 | Johnston et al. |
| 4,770,653 A | 9/1988 | Shturman |
| 4,784,132 A | 11/1988 | Fox et al. |
| 4,785,806 A | 11/1988 | Deckelbaum |
| 4,799,479 A | 1/1989 | Spears |
| 4,862,886 A | 9/1989 | Clarke et al. |
| 4,955,377 A | 9/1990 | Lennox et al. |
| 4,976,711 A | 12/1990 | Parins et al. |
| 5,053,033 A | 10/1991 | Clarke |
| 5,071,424 A | 12/1991 | Reger |
| 5,074,871 A | 12/1991 | Groshong |
| 5,098,429 A | 3/1992 | Sterzer |
| 5,098,431 A | 3/1992 | Rydell |
| 5,102,402 A | 4/1992 | Dror et al. |
| RE33,925 E | 5/1992 | Bales et al. |
| 5,109,859 A | 5/1992 | Jenkins |
| 5,125,928 A | 6/1992 | Parins et al. |
| 5,129,396 A | 7/1992 | Rosen et al. |
| 5,156,151 A | 10/1992 | Imran |
| 5,156,610 A | 10/1992 | Reger |
| 5,158,564 A | 10/1992 | Schnepp-Pesch et al. |
| 5,178,620 A | 1/1993 | Eggers et al. |
| 5,178,625 A | 1/1993 | Groshong |
| 5,190,540 A | 3/1993 | Lee |
| 5,191,883 A * | 3/1993 | Lennox et al. ............... 607/102 |
| 5,211,651 A | 5/1993 | Reger et al. |
| 5,254,098 A * | 10/1993 | Ulrich et al. ................. 604/171 |
| 5,263,493 A | 11/1993 | Avitall |
| 5,277,201 A | 1/1994 | Stern |
| 5,282,484 A | 2/1994 | Reger |
| 5,286,254 A | 2/1994 | Shapland et al. |
| 5,304,121 A * | 4/1994 | Sahatjian ...................... 604/509 |
| 5,304,171 A | 4/1994 | Gregory et al. |
| 5,304,173 A | 4/1994 | Kittrell et al. |
| 5,306,250 A | 4/1994 | March et al. |
| 5,322,064 A | 6/1994 | Lundquist |
| 5,330,518 A | 7/1994 | Neilson et al. |
| 5,345,936 A | 9/1994 | Pomeranz et al. |
| 5,380,319 A | 1/1995 | Saito et al. |
| 5,383,917 A | 1/1995 | Desai et al. |
| 5,409,000 A | 4/1995 | Imran |
| 5,419,767 A | 5/1995 | Eggers et al. |
| 5,453,091 A | 9/1995 | Taylor et al. |
| 5,454,809 A | 10/1995 | Janssen |
| 5,474,530 A | 12/1995 | Passafaro et al. |
| 5,496,311 A | 3/1996 | Abele et al. |
| 5,496,312 A | 3/1996 | Klicek |
| 5,498,261 A | 3/1996 | Strul |
| 5,540,681 A | 7/1996 | Strul et al. |
| 5,545,161 A | 8/1996 | Imran |
| 5,562,100 A | 10/1996 | Kittrell |
| 5,571,122 A | 11/1996 | Kelly et al. |
| 5,571,151 A | 11/1996 | Gregory |
| 5,573,531 A | 11/1996 | Gregory |
| 5,573,533 A | 11/1996 | Strul |
| 5,588,962 A * | 12/1996 | Nicholas et al. .............. 604/507 |
| 5,599,346 A | 2/1997 | Edwards et al. |
| 5,609,606 A | 3/1997 | O'Boyle |
| 5,626,576 A | 5/1997 | Janssen |
| 5,643,297 A | 7/1997 | Nordgren et al. |
| 5,647,847 A | 7/1997 | Lafontaine et al. |
| 5,649,923 A | 7/1997 | Gregory et al. |
| 5,662,671 A | 9/1997 | Barbut et al. |
| 5,665,062 A | 9/1997 | Houser |
| 5,665,098 A | 9/1997 | Kelly et al. |
| 5,681,282 A | 10/1997 | Eggers |
| 5,693,029 A | 12/1997 | Leonhardt |
| 5,693,043 A | 12/1997 | Kittrell et al. |
| 5,697,369 A | 12/1997 | Long, Jr. et al. |
| 5,697,909 A | 12/1997 | Eggers et al. |
| 5,713,942 A | 2/1998 | Stern et al. |
| 5,749,914 A | 5/1998 | Janssen |
| 5,755,753 A | 5/1998 | Knowlton |
| 5,775,338 A | 7/1998 | Hastings |
| 5,776,174 A | 7/1998 | Van Tassel |
| 5,792,105 A | 8/1998 | Lin et al. |
| 5,807,306 A * | 9/1998 | Shapland et al. ................ 604/21 |
| 5,817,092 A | 10/1998 | Behl |
| 5,817,144 A | 10/1998 | Gregory |
| 5,848,969 A | 12/1998 | Panescu et al. |
| 5,860,974 A * | 1/1999 | Abele ............................. 606/41 |
| 5,865,801 A | 2/1999 | Houser |
| 5,869,127 A | 2/1999 | Zhong |
| 5,871,524 A | 2/1999 | Knowlton |
| 5,876,369 A | 3/1999 | Houser |
| 5,876,374 A | 3/1999 | Alba et al. |
| 5,876,397 A | 3/1999 | Edelman et al. |
| 5,904,651 A | 5/1999 | Swanson et al. |
| 5,906,636 A | 5/1999 | Casscells, III et al. |
| 5,919,219 A | 7/1999 | Knowlton |
| 5,934,284 A | 8/1999 | Plaia et al. |
| 5,948,011 A | 9/1999 | Knowlton |
| 5,954,717 A | 9/1999 | Behl et al. |
| 5,999,678 A | 12/1999 | Murphy-Chutorian et al. |
| 6,010,522 A | 1/2000 | Barbut et al. |
| 6,019,757 A | 2/2000 | Scheldrup |
| 6,032,675 A | 3/2000 | Rubinsky |
| 6,033,357 A | 3/2000 | Ciezki et al. |
| 6,033,398 A | 3/2000 | Farley et al. |
| 6,036,689 A | 3/2000 | Tu et al. |
| 6,041,260 A | 3/2000 | Stern et al. |
| 6,050,994 A | 4/2000 | Sherman |
| 6,056,744 A | 5/2000 | Edwards |
| 6,056,746 A | 5/2000 | Goble et al. |
| 6,081,749 A | 6/2000 | Ingle et al. |
| 6,083,159 A | 7/2000 | Driscoll et al. |
| 6,091,995 A | 7/2000 | Ingle et al. |
| 6,117,128 A | 9/2000 | Gregory |
| 6,120,516 A | 9/2000 | Selmon et al. |
| 6,123,702 A | 9/2000 | Swanson et al. |
| 6,123,718 A | 9/2000 | Tu et al. |
| 6,129,725 A | 10/2000 | Tu et al. |
| 6,142,991 A | 11/2000 | Schatzberger |
| 6,152,899 A | 11/2000 | Farley et al. |
| 6,156,046 A | 12/2000 | Passafaro et al. |
| 6,161,048 A | 12/2000 | Sluijter et al. |
| 6,165,187 A | 12/2000 | Reger |
| 6,183,468 B1 | 2/2001 | Swanson et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,561 B1 | 3/2001 | Ramee et al. |
| 6,211,247 B1 | 4/2001 | Goodman |
| 6,216,704 B1 | 4/2001 | Ingle et al. |
| 6,219,577 B1 | 4/2001 | Brown, III et al. |
| 6,228,076 B1 | 5/2001 | Winston et al. |
| 6,231,516 B1 | 5/2001 | Keilman et al. |
| 6,241,727 B1 * | 6/2001 | Tu et al. ........................... 606/41 |
| 6,241,753 B1 | 6/2001 | Knowlton |
| 6,258,087 B1 | 7/2001 | Edwards et al. |
| 6,287,323 B1 | 9/2001 | Hammerslag |
| 6,293,942 B1 | 9/2001 | Goble et al. |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,799 B1 | 12/2001 | Goble |
| 6,328,699 B1 | 12/2001 | Eigler et al. |
| 6,350,276 B1 | 2/2002 | Knowlton |
| 6,353,751 B1 | 3/2002 | Swanson et al. |
| 6,364,840 B1 | 4/2002 | Crowley |
| 6,377,854 B1 | 4/2002 | Knowlton |

(56) References Cited

U.S. PATENT DOCUMENTS

| | | | |
|---|---|---|---|
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,389,311 B1 | 5/2002 | Whayne et al. | |
| 6,389,314 B2 | 5/2002 | Feiring | |
| 6,391,024 B1 | 5/2002 | Sun et al. | |
| 6,394,956 B1 | 5/2002 | Chandrasekaran et al. | |
| 6,405,090 B1 | 6/2002 | Knowlton | |
| 6,409,723 B1 | 6/2002 | Edwards | |
| 6,413,255 B1 | 7/2002 | Stern | |
| 6,421,559 B1 | 7/2002 | Pearlman | |
| 6,423,057 B1 | 7/2002 | He et al. | |
| 6,425,912 B1 | 7/2002 | Knowlton | |
| 6,427,089 B1 | 7/2002 | Knowlton | |
| 6,430,446 B1 | 8/2002 | Knowlton | |
| 6,438,424 B1 | 8/2002 | Knowlton | |
| 6,445,939 B1 | 9/2002 | Swanson et al. | |
| 6,453,202 B1 | 9/2002 | Knowlton | |
| 6,454,775 B1 | 9/2002 | Demarais et al. | |
| 6,458,098 B1 | 10/2002 | Kanesaka | |
| 6,461,378 B1 | 10/2002 | Knowlton | |
| 6,470,216 B1 | 10/2002 | Knowlton | |
| 6,477,426 B1 | 11/2002 | Fenn et al. | |
| 6,482,202 B1 | 11/2002 | Goble et al. | |
| 6,485,489 B2 | 11/2002 | Teirstein et al. | |
| 6,488,679 B1 | 12/2002 | Swanson et al. | |
| 6,497,711 B1 | 12/2002 | Plaia et al. | |
| 6,508,765 B2 | 1/2003 | Suorsa et al. | |
| 6,511,496 B1 | 1/2003 | Huter et al. | |
| 6,522,926 B1 | 2/2003 | Kieval et al. | |
| 6,524,274 B1* | 2/2003 | Rosenthal et al. | 604/96.01 |
| 6,540,761 B2 | 4/2003 | Houser | |
| 6,546,272 B1 | 4/2003 | MacKinnon et al. | |
| 6,552,796 B2 | 4/2003 | Magnin et al. | |
| 6,558,381 B2 | 5/2003 | Ingle et al. | |
| 6,558,382 B2 | 5/2003 | Jahns et al. | |
| 6,569,109 B2 | 5/2003 | Sakurai et al. | |
| 6,569,177 B1 | 5/2003 | Dillard et al. | |
| 6,570,659 B2 | 5/2003 | Schmitt | |
| 6,582,423 B1 | 6/2003 | Thapliyal et al. | |
| 6,589,238 B2 | 7/2003 | Edwards et al. | |
| 6,592,526 B1 | 7/2003 | Lenker | |
| 6,605,061 B2 | 8/2003 | Vantassel et al. | |
| 6,623,453 B1 | 9/2003 | Guibert et al. | |
| 6,632,193 B1 | 10/2003 | Davison et al. | |
| 6,632,196 B1 | 10/2003 | Houser | |
| 6,652,515 B1 | 11/2003 | Maguire et al. | |
| 6,673,066 B2 | 1/2004 | Werneth | |
| 6,673,290 B1 | 1/2004 | Whayne et al. | |
| 6,690,181 B1 | 2/2004 | Dowdeswell et al. | |
| 6,692,490 B1 | 2/2004 | Edwards | |
| 6,695,830 B2 | 2/2004 | Vigil et al. | |
| 6,706,011 B1 | 3/2004 | Murphy-Chutorian et al. | |
| 6,706,037 B2 | 3/2004 | Zvuloni et al. | |
| 6,714,822 B2 | 3/2004 | King et al. | |
| 6,720,350 B2 | 4/2004 | Kunz et al. | |
| 6,723,064 B2 | 4/2004 | Babaev | |
| 6,736,811 B2 | 5/2004 | Panescu et al. | |
| 6,748,953 B2 | 6/2004 | Sherry et al. | |
| 6,760,616 B2 | 7/2004 | Hoey et al. | |
| 6,769,433 B2 | 8/2004 | Zikorus et al. | |
| 6,771,996 B2 | 8/2004 | Bowe et al. | |
| 6,786,904 B2 | 9/2004 | Doscher | |
| 6,788,977 B2 | 9/2004 | Fenn et al. | |
| 6,807,444 B2 | 10/2004 | Tu et al. | |
| 6,829,497 B2 | 12/2004 | Mogul | |
| 6,837,886 B2 | 1/2005 | Collins et al. | |
| 6,845,267 B2 | 1/2005 | Harrison et al. | |
| 6,849,073 B2 | 2/2005 | Hoey et al. | |
| 6,853,425 B2 | 2/2005 | Kim et al. | |
| 6,926,716 B2 | 8/2005 | Baker et al. | |
| 6,932,776 B2 | 8/2005 | Carr | |
| 6,936,047 B2 | 8/2005 | Nasab et al. | |
| 6,953,425 B2 | 10/2005 | Brister | |
| 6,955,174 B2 | 10/2005 | Joye | |
| 6,958,075 B2 | 10/2005 | Mon et al. | |
| 6,962,584 B1 | 11/2005 | Stone | |
| 6,964,660 B2 | 11/2005 | Maguire et al. | |
| 6,972,024 B1 | 12/2005 | Kilpatrick | |
| 6,991,617 B2 | 1/2006 | Hektner et al. | |
| 7,008,667 B2 | 3/2006 | Chudzik et al. | |
| 7,011,508 B2 | 3/2006 | Lum | |
| 7,066,904 B2* | 6/2006 | Rosenthal et al. | 604/103.08 |
| 7,104,987 B2 | 9/2006 | Biggs et al. | |
| 7,137,980 B2 | 11/2006 | Buysse et al. | |
| 7,162,303 B2 | 1/2007 | Levin et al. | |
| 7,192,427 B2 | 3/2007 | Chapelon et al. | |
| 7,200,445 B1 | 4/2007 | Dalbec et al. | |
| 7,252,664 B2 | 8/2007 | Nasab et al. | |
| 7,288,096 B2 | 10/2007 | Chin | |
| 7,291,146 B2 | 11/2007 | Steinke et al. | |
| 7,326,235 B2 | 2/2008 | Edwards | |
| 7,407,671 B2 | 8/2008 | McBride et al. | |
| 7,425,212 B1 | 9/2008 | Danek et al. | |
| 7,426,409 B2 | 9/2008 | Casscells, III et al. | |
| 7,497,858 B2 | 3/2009 | Chapelon et al. | |
| 7,556,624 B2 | 7/2009 | Laufer et al. | |
| 7,617,005 B2 | 11/2009 | Demarais et al. | |
| 7,632,268 B2 | 12/2009 | Edwards et al. | |
| 7,653,438 B2 | 1/2010 | Deem et al. | |
| 7,691,080 B2 | 4/2010 | Seward et al. | |
| 7,717,948 B2 | 5/2010 | Demarais et al. | |
| 7,854,734 B2 | 12/2010 | Biggs et al. | |
| 7,862,565 B2 | 1/2011 | Eder et al. | |
| 7,901,400 B2 | 3/2011 | Wham et al. | |
| 7,942,874 B2 | 5/2011 | Eder et al. | |
| 8,396,548 B2* | 3/2013 | Perry et al. | 604/21 |
| 2001/0051774 A1 | 12/2001 | Littrup et al. | |
| 2002/0062123 A1 | 5/2002 | McClurken et al. | |
| 2002/0072686 A1 | 6/2002 | Hoey et al. | |
| 2002/0077592 A1 | 6/2002 | Barry | |
| 2002/0082552 A1* | 6/2002 | Ding et al. | 604/103.02 |
| 2002/0087156 A1 | 7/2002 | Maguire et al. | |
| 2002/0091381 A1 | 7/2002 | Edwards | |
| 2002/0107511 A1 | 8/2002 | Collins et al. | |
| 2002/0143324 A1 | 10/2002 | Edwards | |
| 2003/0004510 A1 | 1/2003 | Wham et al. | |
| 2003/0028114 A1 | 2/2003 | Casscells, III et al. | |
| 2003/0050635 A1 | 3/2003 | Truckai et al. | |
| 2003/0060857 A1 | 3/2003 | Perrson et al. | |
| 2003/0060858 A1 | 3/2003 | Kieval et al. | |
| 2003/0069619 A1 | 4/2003 | Fenn et al. | |
| 2003/0088189 A1 | 5/2003 | Tu et al. | |
| 2003/0114791 A1 | 6/2003 | Rosenthal et al. | |
| 2003/0195501 A1 | 10/2003 | Sherman et al. | |
| 2003/0212394 A1 | 11/2003 | Pearson et al. | |
| 2003/0220639 A1 | 11/2003 | Chapelon et al. | |
| 2003/0229340 A1 | 12/2003 | Sherry et al. | |
| 2003/0229384 A1 | 12/2003 | Mon | |
| 2004/0006333 A1* | 1/2004 | Arnold et al. | 606/15 |
| 2004/0006359 A1 | 1/2004 | Laguna | |
| 2004/0062852 A1 | 4/2004 | Schroeder et al. | |
| 2004/0064093 A1 | 4/2004 | Hektner et al. | |
| 2004/0073206 A1 | 4/2004 | Foley et al. | |
| 2004/0111016 A1 | 6/2004 | Casscells, III et al. | |
| 2004/0122421 A1 | 6/2004 | Wood | |
| 2004/0181165 A1 | 9/2004 | Hoey et al. | |
| 2004/0186468 A1 | 9/2004 | Edwards | |
| 2004/0220556 A1 | 11/2004 | Cooper et al. | |
| 2004/0243199 A1 | 12/2004 | Mon et al. | |
| 2005/0010208 A1 | 1/2005 | Winston et al. | |
| 2005/0015125 A1 | 1/2005 | Mioduski et al. | |
| 2005/0033136 A1 | 2/2005 | Govari et al. | |
| 2005/0090820 A1 | 4/2005 | Cornelius et al. | |
| 2005/0096647 A1 | 5/2005 | Steinke et al. | |
| 2005/0203434 A1 | 9/2005 | Kassab | |
| 2005/0203498 A1 | 9/2005 | Mon et al. | |
| 2005/0251116 A1 | 11/2005 | Steinke et al. | |
| 2005/0283195 A1 | 12/2005 | Pastore et al. | |
| 2006/0085054 A1 | 4/2006 | Zikorus et al. | |
| 2006/0089638 A1 | 4/2006 | Carmel | |
| 2006/0149166 A1 | 7/2006 | Zvuloni | |
| 2006/0184060 A1 | 8/2006 | Belalcazar et al. | |

(56) References Cited

U.S. PATENT DOCUMENTS

| | | |
|---|---|---|
| 2006/0235286 A1* | 10/2006 | Stone et al. .................. 600/381 |
| 2006/0246143 A1 | 11/2006 | Ege |
| 2006/0280858 A1* | 12/2006 | Kokish ........................ 427/2.1 |
| 2007/0078498 A1 | 4/2007 | Rezai et al. |
| 2007/0173805 A1 | 7/2007 | Weinberg et al. |
| 2007/0173899 A1 | 7/2007 | Levin et al. |
| 2007/0197891 A1 | 8/2007 | Shachar et al. |
| 2007/0265687 A1 | 11/2007 | Deem et al. |
| 2007/0278103 A1 | 12/2007 | Hoerr et al. |
| 2008/0125772 A1 | 5/2008 | Stone et al. |
| 2008/0140002 A1 | 6/2008 | Ramzipoor et al. |
| 2008/0161801 A1 | 7/2008 | Steinke et al. |
| 2008/0188912 A1 | 8/2008 | Stone et al. |
| 2008/0188913 A1 | 8/2008 | Stone et al. |
| 2008/0262489 A1 | 10/2008 | Steinke |
| 2009/0018609 A1 | 1/2009 | DiLorenzo |
| 2009/0062873 A1 | 3/2009 | Wu et al. |
| 2009/0074828 A1 | 3/2009 | Alexis et al. |
| 2010/0076299 A1 | 3/2010 | Gustus et al. |
| 2010/0125239 A1 | 5/2010 | Perry et al. |
| 2010/0125268 A1 | 5/2010 | Gustus et al. |
| 2010/0137952 A1 | 6/2010 | Demarais et al. |
| 2010/0160906 A1 | 6/2010 | Jarrard |
| 2010/0204560 A1 | 8/2010 | Salahieh et al. |
| 2010/0249702 A1* | 9/2010 | Magana et al. .......... 604/103.01 |
| 2010/0286684 A1 | 11/2010 | Hata et al. |
| 2010/0324472 A1 | 12/2010 | Wulfman |
| 2011/0092880 A1 | 4/2011 | Gertner |
| 2011/0104061 A1 | 5/2011 | Seward |
| 2011/0118598 A1 | 5/2011 | Gertner |
| 2011/0118600 A1 | 5/2011 | Gertner |
| 2011/0118726 A1 | 5/2011 | De La Rama |
| 2011/0178403 A1 | 7/2011 | Weng et al. |
| 2011/0207758 A1 | 8/2011 | Sobotka |
| 2011/0270238 A1 | 11/2011 | Rizq et al. |
| 2011/0306851 A1 | 12/2011 | Wang |
| 2011/0307034 A1 | 12/2011 | Hastings et al. |
| 2011/0319809 A1 | 12/2011 | Smith |
| 2012/0029496 A1 | 2/2012 | Smith |
| 2012/0029500 A1 | 2/2012 | Jenson |
| 2012/0029509 A1 | 2/2012 | Smith |
| 2012/0029511 A1 | 2/2012 | Smith |
| 2012/0029512 A1 | 2/2012 | Willard et al. |
| 2012/0157987 A1 | 6/2012 | Steinke et al. |
| 2012/0157989 A1 | 6/2012 | Stone et al. |
| 2012/0158101 A1 | 6/2012 | Stone et al. |

FOREIGN PATENT DOCUMENTS

| | | |
|---|---|---|
| CN | 102271607 A | 12/2011 |
| DE | 102005041601 A1 | 4/2007 |
| DE | 102008048616 A1 | 4/2010 |
| EP | 558297 A2 | 9/1993 |
| EP | 647435 A1 | 4/1995 |
| EP | 634910 B1 | 8/1997 |
| EP | 868884 A2 | 10/1998 |
| EP | 1005838 A1 | 6/2000 |
| EP | 1053720 A1 | 11/2000 |
| EP | 1064886 A1 | 1/2001 |
| EP | 1181895 A2 | 2/2002 |
| EP | 1297795 A1 | 6/2002 |
| EP | 1264613 A2 | 12/2002 |
| EP | 1286625 A1 | 3/2003 |
| EP | 1332724 A1 | 8/2003 |
| EP | 866675 B1 | 10/2003 |
| EP | 1433448 A1 | 6/2004 |
| EP | 1442719 A1 | 8/2004 |
| EP | 1547537 A1 | 6/2005 |
| EP | 1622531 | 2/2006 |
| EP | 1634542 A1 | 3/2006 |
| EP | 1698296 A1 | 6/2006 |
| EP | 1709922 A1 | 10/2006 |
| EP | 1946712 A1 | 7/2008 |
| EP | 1961394 A2 | 8/2008 |
| EP | 1715798 B1 | 4/2009 |
| EP | 2092957 A1 | 8/2009 |
| EP | 2208506 A1 | 7/2010 |
| EP | 2241279 A1 | 10/2010 |
| EP | 2329859 A1 | 6/2011 |
| GB | 2313062 A | 11/1997 |
| GB | 2453601 A | 4/2009 |
| JP | 1995-213621 A | 8/1995 |
| JP | 1995-313603 A | 12/1995 |
| JP | 2003-510126 A | 3/2003 |
| WO | WO 91/03207 A1 | 3/1991 |
| WO | WO 91/17731 A1 | 11/1991 |
| WO | WO 92/22239 A1 | 12/1992 |
| WO | WO 93/20747 A1 | 10/1993 |
| WO | WO 93/20770 A2 | 10/1993 |
| WO | WO 94/18896 A1 | 9/1994 |
| WO | WO 94/28809 A1 | 12/1994 |
| WO | WO 95/01751 A1 | 1/1995 |
| WO | WO 95/31142 A1 | 11/1995 |
| WO | WO 96/34559 A1 | 11/1996 |
| WO | WO 97/03604 A1 | 2/1997 |
| WO | WO 97/17104 A1 | 5/1997 |
| WO | WO 97/20510 A1 | 6/1997 |
| WO | WO 97/32532 A1 | 9/1997 |
| WO | WO 97/40760 A1 | 11/1997 |
| WO | WO 97/45156 A2 | 12/1997 |
| WO | WO 98/18393 A1 | 5/1998 |
| WO | WO 98/29030 A1 | 7/1998 |
| WO | WO 98/34565 A1 | 8/1998 |
| WO | WO 98/35638 A1 | 8/1998 |
| WO | WO 98/40023 A1 | 9/1998 |
| WO | WO 99/00060 A1 | 1/1999 |
| WO | WO 99/16370 A1 | 4/1999 |
| WO | WO 99/21608 A1 | 5/1999 |
| WO | WO 99/34741 A1 | 7/1999 |
| WO | WO 99/44522 A1 | 9/1999 |
| WO | WO 00/01313 A1 | 1/2000 |
| WO | WO 00/10475 A1 | 3/2000 |
| WO | WO 00/51513 A1 | 9/2000 |
| WO | WO 00/59394 A1 | 10/2000 |
| WO | WO 00/62727 A1 | 10/2000 |
| WO | WO 00/64387 A1 | 11/2000 |
| WO | WO 00/69376 A1 | 11/2000 |
| WO | WO 00/72909 A1 | 12/2000 |
| WO | WO 01/22897 A1 | 4/2001 |
| WO | WO 01/37746 A1 | 5/2001 |
| WO | WO 01/87172 A1 | 5/2001 |
| WO | WO 01/74255 A | 10/2001 |
| WO | WO 01/87154 A1 | 11/2001 |
| WO | WO 01/95820 A1 | 12/2001 |
| WO | WO 02/15807 A1 | 2/2002 |
| WO | WO 02/28475 A1 | 4/2002 |
| WO | WO 02/39915 A1 | 5/2002 |
| WO | WO 02/058549 A1 | 8/2002 |
| WO | WO 02/080766 A2 | 10/2002 |
| WO | WO 02/087679 A2 | 11/2002 |
| WO | WO 02/089686 A1 | 11/2002 |
| WO | WO 03/077781 A1 | 9/2003 |
| WO | WO 2004/047659 A2 | 6/2004 |
| WO | WO 2004/049976 A1 | 6/2004 |
| WO | WO 2004/064606 A2 | 8/2004 |
| WO | WO 2004/069300 A2 | 8/2004 |
| WO | WO 2004/076146 A2 | 9/2004 |
| WO | WO 2004/098694 A1 | 11/2004 |
| WO | WO 2004/105807 A2 | 12/2004 |
| WO | WO 2005/007000 | 1/2005 |
| WO | WO 2005/037070 A2 | 4/2005 |
| WO | WO 2005/041748 A2 | 5/2005 |
| WO | WO 2005/074829 A1 | 8/2005 |
| WO | WO 2006/041881 A2 | 4/2006 |
| WO | WO 2006/105121 A2 | 10/2006 |
| WO | WO 2006/116198 A2 | 11/2006 |
| WO | WO 2007/011634 A1 | 1/2007 |
| WO | WO 2007/014063 A2 | 2/2007 |
| WO | WO 2007/047870 A2 | 4/2007 |
| WO | WO 2007/113865 A1 | 10/2007 |
| WO | WO 2007/135431 A2 | 11/2007 |
| WO | WO 2007/146215 A2 | 12/2007 |
| WO | WO 2008/003058 A2 | 1/2008 |

(56) References Cited

FOREIGN PATENT DOCUMENTS

| | | |
|---|---|---|
| WO | WO 2008/009972 A2 | 1/2008 |
| WO | WO 2008/010150 A2 | 1/2008 |
| WO | WO 2008/036281 A2 | 3/2008 |
| WO | WO 2008/049084 A2 | 4/2008 |
| WO | WO 2008/061152 A2 | 5/2008 |
| WO | WO 2008/102363 A2 | 8/2008 |
| WO | WO 2009/036471 A1 | 3/2009 |
| WO | WO 2009/082635 A1 | 7/2009 |
| WO | WO 2009/088678 A1 | 7/2009 |
| WO | WO 2009/113064 A2 | 9/2009 |
| WO | WO 2009/121017 | 10/2009 |
| WO | WO 2009/137819 A1 | 11/2009 |
| WO | WO 2010/042653 A1 | 4/2010 |
| WO | WO 2010/048007 A1 | 4/2010 |
| WO | WO 2010/056771 A1 | 5/2010 |
| WO | WO 2010/057043 A1 | 5/2010 |
| WO | WO 2010/070766 A1 | 6/2010 |
| WO | WO 2010/099207 A1 | 9/2010 |
| WO | WO 2010/120944 A2 | 10/2010 |
| WO | WO 2010/134503 A1 | 11/2010 |
| WO | WO 2011/055143 A2 | 5/2011 |
| WO | WO 2011/060339 A1 | 5/2011 |
| WO | WO 2011/126580 A2 | 10/2011 |

OTHER PUBLICATIONS

Tepe et al., "Local Delivery of Paclitaxel to Inhibit Restenosis During Angioplasty of the Leg," N Engl J Med, Feb. 14, 2008; 358(7): 689-699; retrieved from the Internet: <<http://content.nejm.org/cgi/reprint/358/7/689.pdf>>.

International Search Report and Written Opinion of PCT Application No. PCT/US09/64465, mailed Jan. 13, 2010, 13 pages total.

U.S. Appl. No. 10/938,138, filed Sep. 10, 2004, Pat. No. 7,291,146, Issued Nov. 6, 2007.

U.S. Appl. No. 11/684,779, filed Sep. 28, 2007.

U.S. Appl. No. 13/403,920, filed Feb. 23, 2012.

U.S. Appl. No. 11/122,263, filed May 3, 2005.

U.S. Appl. No. 11/392,231, filed Mar. 28, 2006, Pat. No. 7,742,795, Issued Jun. 22, 2010.

U.S. Appl. No. 12/660,515, filed Feb. 26, 2010.

U.S. Appl. No. 13/406,458, filed Feb. 27, 2012.

U.S. Appl. No. 11/975,651, filed Oct. 18, 2007.

U.S. Appl. No. 13/408,135, filed Feb. 29, 2012.

U.S. Appl. No. 12/150,095, filed Apr. 23, 2008.

U.S. Appl. No. 12/617,519, filed Nov. 12, 2009.

U.S. Appl. No. 11/975,474, filed Oct. 18, 2007.

U.S. Appl. No. 13/385,540, filed Feb. 24, 2012.

U.S. Appl. No. 11/975,383, filed Oct. 18, 2007.

U.S. Appl. No. 13/385,555, filed Feb. 24, 2012.

U.S. Appl. No. 12/616,720, filed Nov. 11, 2009.

U.S. Appl. No. 12/564,268, filed Feb. 22, 2009.

U.S. Appl. No. 13/066,347, filed Apr. 11, 2011.

Brown et al., "Radiofrequency capacitive heaters: the effect of coupling medium resistivity on power absorption along a mouse leg" Phys Med Biol 1993, 38 1-12 (abstract).

Cardiovascular Technologies, Inc., "Heated Balloon Device Technology" [Presentation], 2007-2008, 11 pages total. Retrieved from: <<http://www.cvtechinc.com/pr/presoCVT_Heated_Balloon_Tech.pdf>>.

Carrington, "Future of CVI: It's All About the Plaque." Diagnostic Imaging Special Edition Forum [online] [retrieved on Sep. 03, 2003] Retrieved from the Internet:,http://dimag.com/specialedition/cardiacimg.shtml> 5 pages total.

Cimino, "Preventing Plaque Attack", [online] [retrieved on Sep. 3, 2003] Retrieved from the Internet: <http://Masshightech.com/displayarticledetail.ap?art_id=52283&cat_id=10>, 3 pages total.

Dahm et al, "Relation of Degree of Laser Debulking of In-Stent Restenosis as a Predictor of Restenosis Rate", Am J Cardiol, 2002; 90(1): 68-70.

De Korte C L. et al., "Characterization of Placque Components with Intravascular Ultrasound Elastography in Human Femoral and Coronary Arteries In Vitro," Circulation 2000;102:617-623.

Durney C., et al., Radiofrequency Radiation Dosimetry Handbook (with table of contents), Oct. 1986, 4th ed., 7 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/handbook/home.htm.

Fournier-Desseux et al. "Assessment of 1-lead and 2-lead electrode patterns in electrical impedance endotomography", Physiol. Meas. (2005) 26:337-349.

Fujimori et al., "Significant Prevention of In-Stent Restenosis by Evans Blue in Patients with Acute Myocardial Infarction", Abstract #2925, AHA (2002), 1 page total.

Fujita, "Sarpogrelate, An Antagonist of 5-$HT_{2a}$ Receptor Treatment Reduces Restenosis After Coronary Stenting", Abstract #2927, AHA (2002), 1 page total.

Gabriel C, et al., Compilation of the Dielectric Properties of Body Tissues at RF and Microwave Frequencies (with table of contents), Jun. 1996, 17 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Report/Report.html.

Gabriel C, et al., Compilation of the Dielectric Properties of Body Tissues at RF and Microwave Frequencies, Appendi0410-2009 A, Jun. 1996, 21 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009.A/Appendi04-10-2009 A.html.

Gabriel C, et al., Compilation of the Dielectric Properties of Body Tissues at RF and Microwave Frequencies, Appendi04-10-2009 C, Jun. 1996, 6 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009.C/Appendi04-10-2009 C.html.

Gregory et al., "Liquid Core Light Guide for Laser Angioplasty", Journal of Quantum Electronics, vol. 26, No. 12, (Dec. 1990), pp. 2289-2296.

Intraluminal, Product description [online] [retrieved on Sep. 3, 2003] Retrieved from the Internet: http://www.intraluminal.com/products/inde04-10-2009 .html> 1 page total.

Kaplan et al., "Healing after arterial dilatation with radiofrequency thermal and nonthermal balloon angioplasty systems," J Invest Surg. Jan.-Feb. 1993;6(1):33-52.

Kolata, "New Studies Question Value of Opening Arteries", New York Times [online] [retrieved on Jan. 25, 2005]. Retrieved from the Internet: <http://nytimes.com/2004/03/21/health/21HEAR.html?ei=5070&en=641bc03214e&e04-10-2009 =11067>, 5 pages total.

Konings M K, et al., "Development of an Intravascular Impedance Catheter for Detection of Fatty Lesions in Arteries," IEEE Transactions on Medical Imaging, vol. 51, No. 4, Apr. 2004.

Kurtz et al., "Lamellar Refractive Surgery with Scanned Intrastromal Picosecond and Femtosecond Laser Pulses in Animal Eyes", J Refract Surg, vol. 14, (Sep./Oct. 1998), pp. 541-548.

Lightlab Imaging Technology, "Advantages of OCT", [online] [retrieved on Sep. 3, 2003]. Retrieved from the Internet: <http:www.lightlabimaging.com/advantage.html> 2 pages total.

Lightlab Imaging Technology, "Image Gallery", [online] [retrieved on Sep. 3, 2003]. Retrieved from the Internet: <http:lightlabimaging.com/gallery/cvpstill.html> 4 pages total.

Lightlab Imaging Technology, "LightLab Imaging Starts US Cardiology Clinical Investigations", LightLab Company Press Release, [online] [retrieved on Sep. 3, 2003]. Retrieved from the Internet: <http://www.lighlabimaging.com/press/cardtrails.html> 2 pages total.

(56) References Cited

OTHER PUBLICATIONS

Lightlab Imaging Technology, "LightLab Sees Bright Prospects for Cardiac Application of OCT Technology" *The Graysheet Medical Devices Diagnostics & Instrumentation*, vol. 27, No. 35, (Aug. 27, 2001) [online] [retrieved on Sep. 3, 2003]. Retrieved from the Internet: <http://www.lighlabimaging.com/press/graysheet.html> 1 page total.
Lightlab Imaging Technology, "What is OCT?", [online] [retrieved on Sep. 3, 2003]. Retrieved from the Internet: <http:lightlabimaging.com/oct.html.> 2 pages total.
Lightlab Imaging Technology, "Why use OCT?", [online] [retrieved on Sep. 3, 2003]. Retrieved from the Internet: <http:lightlabimaging.com/whyoct.html> 2 pages total.
Lima et al., "Efficacy and Safety of Oral Sirolimus to Treat and Prevent In-Stent Restenosis: A Pilot Study Results", Abstract #2929, *AHA* (2002), 1 page total.
Lima et al., "Systemic Immunosuppression Inhibits In-Stent Coronary Intimal Proliferation in Renal Transplant Patients", Abstract #2928, *AHA* (2002), 1 page total.
MIT Techtalk, "Laser Catheter to Aid Coronary Surgery", Jan. 9, 1991 [online] [retrieved on Feb. 7, 2005]. Retrieved from the Internet : <http://web.mit.edu/newsoffice/tt/1991/jan09/24037.html> 4 pages total.
Morice et al., "A Randomized Comparison of a Sirolimus-Eluting Stent With a Standard Stent for Coronary Revascularization", *N. Engl J Med*, vol. 346, No. 23, (Jun. 6, 2002), pp. 1773-1779.
Müller et al., "Effectiveness and Safety of Ultrasonic Atherosclerotic Plaque Ablation: in Vitro Investigation", *CardioVas. Intervent. Radiol.*, (1993) 16: 303-307.
Nair A, et al., "Regularized Autoregressive Analysis of Intravascular Ultrasound Backscatter: Improvement in Spatial Accuracy of Tissue Maps," IEEE Transactions on Ultrasonics, Ferroelectrics, and Frequency Control, vol. 51 No. 4, Apr. 2004.
Popma et al., "Chapter 38—Percutaneous Coronary and Valvular Intervention", Heart Disease: A Textbook of Cardiovascular Medicine, 6th ed., (2001) W.B> Saunders Company, pp. 1364-1405.
Romer et al., "Histopathology of Human Coronary Atherosclerosis by Quantifying Its Chemical Composition with Raman Spectroscopy," Circulation 97:878-885 (1998).
Scheller, "Intracoronary Paclitaxel Added to Contrast Media Inhibits In-Stent Restenosis of Porcine Coronary Arteries", Abstract #2227, *AHA* (2002), 2 pages total.
Shaffer, "Scientific Basis of Laser Energy", *Clin Sports Med* 2002; 21(4):585-598.
Shmatukha aA V, et al., "MRI temperature mapping during thermal balloon angioplasty," Phys Med Biol 51, (2006) N163-N171.
Slager et al., "Vaporization of Atherosclerotic Placques by Spark Erosion," J Am Coll Cardiol, vol. 5 (Jun. 1985) pp. 1382-1386.
Stiles et al., "Simulated Charactization of Atherosclerotic Lesions in the Coronary Arteries by Measurement of Bioimpedance," IEEE Transactions on Biomedical Engineering, (Jul. 2003), 5(4):916-921.
Süselbeck et al. "Intravascular electric impedance spectroscopy of atherosclerotic lesions using a new impedance system", Basic Res Cardiol (2005) 100:446-452.
Suselbeck T, et al., "In vivo intravascular electrical impedance spectroscopy using a new catheter with integrated microelectrodes," Basic Res Cardiol 100:28-34 (2005).
Van Den Berg, "Light Echoes Image the Human Body", *OLE*, Oct. 2001, pp. 35-37.
Volcano Therapeutics, "Product—Functional Measurement", [online] [retrieved on Sep. 3, 2003]. Retrieved from the Internet: <http://www.volcanotherapeutics.com/pages/products/functional_measurement-us.html> 2 pages total.
Examiner's Report of Canadian Patent Application No. 2,539,026, mailed Feb. 6, 2012, 4 pages total.
Office Action issued in Chinese Patent Application No. 200480030163.9, mailed Jan. 16, 2009, 8 pages total.
Office Action issued in Chinese Patent Application No. 200480030163.9, mailed Mar. 28, 2008, 7 pages total.
Office Action issued in Chinese Patent Application No. 200480030163.9, mailed Aug. 31, 2007, 8 pages total.
Office Action issued in Chinese Patent Application No. 200480030163.9, mailed Jul. 31, 2009, 5 pages total.
Supplementary Partial European Search Report of Application No. 04816863.7, mailed May 8, 2009, 7 pages total.
Office Action issued in European Application No. 04816863.7, mailed Jun. 4, 2010, 5 pages total.
Office Action issued in European Application No. 04816863.7, mailed Dec. 5, 2011, 4 pages total.
Office Action issued in European Application No. 04816863.7, mailed Jan. 22, 2010, 6 pages total.
Formal Inquiry issued in Japanese Patent Application No. 2006-526351, mailed Jan. 17, 2012, 5 pages total.
Notice of the Reason for Refusal issued in Japanese Patent Application No. 2006-526351, mailed Apr. 27, 2010, 6 pages total.
Final Decision of Rejection issued in Japanese Patent Application No. 2006-526351, mailed Jan. 18, 2011, 4 pages total.
European Search Report and Search Opinion of EP Patent Application No. 12151957.3, mailed Apr. 16, 2012, 8 pages total.
Office Action issued in Chinese Patent Application No. 200680016424.0, mailed Apr. 13, 2010, 10 pages total.
European Search Report and Search Opinion of EP Patent Application No. 06748830.4, mailed Nov. 16, 2009, 12 pages total.
Partial European Search Report of EP Patent Application No. 11191822.3, mailed Mar. 19, 2012, 7 pages total.
Office Action issued in Chinese Patent Application No. 201110031923.X, mailed Nov. 17, 2011, 16 pages total.
Office Action issued in Chinese Patent Application No. 201110031923.X, mailed May 22, 2012, 10 pages total.
Examiner's First Report of Australian Patent Application No. 2007310988, mailed May 23, 2012, 4 pages total.
European Search Report and Search Opinion of EP Patent Application No. 07844421.3, mailed Jan. 4, 2010, 15 pages total.
European Search Report and Search Opinion of EP Patent Application No. 12155447.1, mailed May 10, 2012, 6 pages total.
International Search Report and Written Opinion of PCT Application No. PCT/US2009/064027, mailed Jan. 19, 2010, 9 pages total.
European Search Report and Search Opinion of EP Patent Application No. 07844417.1, mailed Nov. 5, 2009.
European Search Report and Search Opinion of EP Patent Application No. 12154120.5, mailed May 8, 2012, 8 pages total.
European Search Report and Search Opinion of EP Patent Application No. 07844424.7, mailed Nov. 11, 2009, 11 pages total.
Partial European Search Report of EP Patent Application No. 12154069.4, mailed May 10, 2012, 5 pages total.
International Search Report and Written Opinion of PCT Application No. PCT/US2009/064465, mailed Jan. 13, 2010, 13 pages total.
International Search Report of PCT Application No. PCT/US09/57728, mailed Nov. 30, 2009, 10 pages total. (2410PC).
International Search Report and Written Opinion of PCT/US2011/00661, mailed Nov. 18, 2011, 14 pages total.
International Search Report directed to PCT/US2010/034789, mailed Jul. 9, 2010, 2 pages total.
Written Opinion directed to PCT/US2010/034789, mailed Jul. 9, 2010, 11 pages total.
Notice of the Reason for Refusal issued in Japanese Patent Application No. 2009-533544, mailed Jun. 19, 2012, 3 pages total.
Summons to Attend Oral Proceedings of EP Patent Application No. 07844424.7, mailed Jul. 5, 2012, 7 pages total.
European Search Report and Search Opinion of EP Patent Application No. 11191822.3, mailed Jun. 13, 2012, 13 pages total.
Office Action issued in European Application No. 07844421.3, mailed Aug. 23, 2012, 5 pages total.
Notice of the Reason for Refusal issued in Japanese Patent Application No. 2009-533546, mailed Jun. 19, 2012, 6 pages total.
Extended European Search Report and Search Opinion of EP Patent Application No. 12154069.4, mailed Sep. 17, 2012, 13 pages total.
Brown et al., "Observations on the shrink temperature of collagen and its variations with age and disease," Ann Rheum Dis, Jun. 1, 1958, 17(2):196-208.

(56) References Cited

OTHER PUBLICATIONS

Notice of the Reason for Refusal issued in Japanese Patent Application No. 2006-526351, mailed Sep. 18, 2012, 20 pages total.

Office Action issued in Chinese Patent Application No. 201110031923.X, mailed on Sep. 6, 2012, 11 pages total.

Office Action issued in Australian Patent Application No. 2010248955, mailed Sep. 13, 2012, 4 pages total.

* cited by examiner

DIRECTIONAL DELIVERY OF ENERGY AND BIOACTIVES

CROSS-REFERENCES TO RELATED APPLICATIONS

The present application claims the benefit under 35 USC 119(e) of U.S. Provisional Application No. 61/177,744 filed May 13, 2009; the full disclosure of which is incorporated herein by reference in its entirety.

The subject matter of the subject application is related to that of Provisional Application Ser. No. 61/114,958 filed Nov. 14, 2008 and U.S. patent application Ser. No. 12/616,720 filed Nov. 11, 2009; the full disclosure of which is also incorporated herein by reference.

BACKGROUND OF THE INVENTION

1. Field of the Invention

The present invention is generally related to medical devices, systems, and methods. In particular, the invention provides methods and systems for delivery of energy and/or bioactive materials (i.e. bioactives) to body tissue, most preferably by selective delivery to body tissues disposed about a lumen using a catheter-based treatment system.

2. Discussion of Related Art

Physicians use catheters to gain access to, and repair interior tissues of the body, particularly within the lumens of the body such as blood vessels. For example, balloon angioplasty and other catheters often are used to open arteries that have been narrowed due to atherosclerotic disease. Balloon angioplasty is often effective at opening an occluded blood vessel, but the trauma associated with balloon dilation can impose significant injury, so that the benefits of balloon dilation may be limited in time.

Stenting procedures, in conjunction with balloon dilation, are often the preferred treatments for atherosclerosis. In stenting, a collapsed metal framework is mounted on a balloon catheter, which is introduced into the body. The stent is manipulated into the site of occlusion and expanded in place by the dilation of the underlying balloon, or in the example of a self-expanding stent, the stent scaffolds open upon release of constraint by the catheter. Stenting has gained widespread acceptance, and produces generally acceptable results in many cases. Along with treatment of blood vessels (particularly the coronary arteries), stents can also be used in treating many other tubular obstructions within the body, such as for treatment of reproductive, gastrointestinal, and pulmonary obstructions. Restenosis or a subsequent narrowing of the body lumen after stenting has occurred in a significant number of cases.

A variety of modified restenosis treatments or restenosis-inhibiting treatment modalities have also been proposed, including intravascular radiation, cryogenic treatments, ultrasound energy, and the like, often in combination with balloon angioplasty and/or stenting. While these and different approaches show varying degrees of promise for decreasing the subsequent degradation in blood flow following angioplasty and stenting, the trauma initially imposed on the tissues by angioplasty remains problematic.

A number of alternatives to stenting and balloon angioplasty have been proposed to open stenosed arteries. For example, a wide variety of atherectomy devices and techniques have been disclosed and attempted. Despite the disadvantages and limitations of angioplasty and stenting, atherectomy has not gained the widespread use and success rates of dilation-based approaches. More recently, still further disadvantages of dilation have come to light. These include the existence of vulnerable plaque, which can rupture and release materials that may cause myocardial infarction or heart attack.

More recently, drug coated stents (such as Johnson and Johnson's Cypher stent, the associated drug comprising Sirolimus) have demonstrated a markedly reduced restenosis rate, and others are developing and commercializing alternative drug eluting stents. While drug-eluting stents appear to offer significant promise for treatment of atherosclerosis in many patients, there remain many cases where stents either cannot be used or present significant disadvantages. Generally, stenting leaves an implant in the body. Such implants can present risks, including mechanical fatigue, corrosion, thrombus formation, and the like, particularly when removal of the implant is difficult and involves invasive surgery. Stenting may have additional disadvantages for treating diffuse artery disease, for treating bifurcations, for treating areas of the body susceptible to crush, and for treating arteries subject to torsion, bending, elongation, and shortening.

Information that may be relevant to proposed treatments of atherosclerotic disease can be found in U.S. Pat. Nos. 5,102,402; 5,304,121; 5,304,171; 5,306,250; 5,380,319; 5,588,962; 5,693,029; 6,389,314; 6,477,426; 6,623,453; 6,695,830; 6,706,011; 6,723,064; 6,788,977; 6,991,617; 6,958,075; 7,008,667; 7,066,904; 7,291,146; and 7,407,671, for example. Further information can be found in U.S. Patent Application Publication Nos. 2003/0069619; 2003/0229384; 2004/0062852; 2004/0243199; 2005/0203498; 2005/0251116; 2005/0283195; 2006/0235286; 2007/0278103; 2008/0125772; 2008/0140002; 2008/0161801; 2008/0188912; 2008/0188913; 2008/0262489 and 2009/0074828 as well as European Patent Application No. EP 1622531 and PCT Patent Publication Nos. WO 2005/007000 and WO 2009/121017. Scheller et al., "Potential Solutions to the Current Problem: Coated Balloon," *EuroIntervention*, 2008 Aug.; 4 Suppl C: C63-66 and Tepe et al., "Local Delivery of Paclitaxel to Inhibit Restenosis During Angioplasty of the Leg," *N Engl J Med*, 2008 Feb. 14; 358(7): 689-699 may also include relevant information.

Therefore, it would be advantageous to provide new and/or improved methods and systems for delivery of therapeutic treatment to diseased tissue. Ideally, these improved techniques would facilitate selectively targeting tissue for treatment through the introduction of temperature change and/or bioactives to the targeted tissue in such a way that may simplify the procedure, may reduce procedure time, may improve the therapeutic result, or any combination thereof.

BRIEF SUMMARY OF THE INVENTION

The present invention relates to the treatment of targeted tissue by directionally delivering energy and/or bioactive materials in order to achieve a therapeutic effect. In the most preferred embodiment a balloon catheter system having a balloon portion, further comprised of a plurality of electrodes, may be energized to selectively deliver energy, bioactives, or a combination thereof to targeted tissue. Tissue may be targeted by applying energy, making tissue impedance analysis, and further selectively energizing electrodes through the use of an energy source with a controller.

In a preferred embodiment, a system for the treatment of a target tissue by directionally delivering energy and/or bioactive material comprises an elongate catheter having a proximal end and a distal end with an axis therebetween. The catheter has a radially expandable balloon near the distal end and an energy delivery surface on the balloon. A thermally changeable coating with a releasable bioactive material is coupled to the balloon. The thermally changeable coating is oriented to be urged against the target tissue when the balloon expands. An energy source is operatively coupled to the catheter to energize the energy delivery surface to heat the thermally changeable coating and release the bioactive material to the target tissue.

In another embodiment, the energy delivery surface comprises a plurality of spaced electrodes disposed about the expandable balloon. The energy source is operatively coupled to the plurality of electrodes to selectively energize the electrode pairs to heat portions of the thermally changeable coating between the electrode pairs to release the bioactive material to the target tissue.

In an exemplary embodiment, the electrodes are coated with an insulating material.

In yet another embodiment, the balloon is encapsulated by a selectively permeable membrane overlaid by a plurality of circumferentially spaced electrodes.

In another embodiment, the balloon is configured to receive inflation media comprising bioactive material.

In some embodiments, a tissue analyzer is configured to characterize the body tissue.

In other embodiments, the electrode delivery portion is energized to heat the thermally changeable coating to release the bioactive material in response to the characterized body tissue.

In another embodiment, the electrode delivery portion is energized to heat the body tissue before, during and/or after the delivery of the bioactive material.

In another embodiment, the thermally changeable coating includes more than one releasable bioactive material. Each material may have a different phase change temperature.

In another embodiment, the bioactive material is selected from at least one of an antiproliferative, an antithrombin, an immunosuppressant, a lipid, an anti-lipid, a liposome, an anti-inflamatory, an antineoplastic, an antiplatelet, an angiogenic agent, an anti-angiogentic agent, a vitamin, an aptamer, an antimitotic, a metalloproteinase inhibitor, a NO donor, an estradiol, an anti-sclerosing agent, a vasoactive, a growth factor, a beta blocker, an AZ blocker, a hormone, a statin, an antioxidant, a membrane stabilizing agent, a calcium antagonist, a retinoid, a peptide, a lipoprotein, a polypeptide, a polynucleotide encoding polypeptides, a protein, a protein drug, an enzyme, a genetic material, a cell, a chemical solvent, an energy-activated agent, an anti-lymphocyte, an anti-macrophage substance or a combination of any of the above.

In yet another embodiment, the bioactive material is attached to a portion of a liposome.

In another embodiment, the thermally changeable coating is selected from at least one of, polylactic acid, polyglycolic acid, polyvinyl acetate, polyvinyl propylene, hydroxypropyl methylcellulose, methacrylate or a combination of any of the above.

In other embodiments, the energy source is a RF energy source and the delivery portion is configured to transmit RF energy to release and/or activate at least one bioactive material.

In other embodiments, the energy source is a light energy source and the delivery portion is configured to transmit light energy to release and/or activate at least one bioactive material.

In an exemplary embodiment, a method for the selective delivery of a releasable bioactive material includes engaging a body tissue disposed about a lumen with a thermally changeable coating by radially expanding a balloon of a catheter. The thermally changeable coating is disposed on the balloon. A surface on the balloon is energized to heat the thermally changeable coating. The bioactive material is released from the thermally changeable coating into the body tissue in response to the heating.

In another embodiment, the delivery portion comprises a plurality of electrodes disposed about the expandable balloon and select electrode pairs are energized to heat and liquefy portions of the thermally changeable coating between the electrode pairs.

In yet another embodiment, the body tissue of the lumen includes a diseased portion. Select electrode pairs are energized to heat the thermally changeable coating proximate the diseased portion.

In another embodiment, tissue is characterized to identify body tissue to be treated. Portions of the thermally changeable coating are selectively heated to release the bioactive material in response to the characterized body tissue to treat the identified body tissue.

In another embodiment, the body tissue is heated before, during and/or after the delivery of the bioactive material. The bioactive material is selected from at least one of a therapeutic fluid, an anesthetic drug, a therapeutic drug, a small molecule, a gene therapeutic compound, an anti-thrombolytic agent, a lubricant to allow higher temperatures without sticking, an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

In another embodiment, the delivery portion is energized with RF energy to release and/or activate at least one bioactive material.

In another embodiment, the delivery portion is energized with laser energy to release and/or activate at least one bioactive material.

In another embodiment, the delivery portion is energized with ultrasound energy to release and/or activate at least one bioactive material.

In another embodiment, the delivery portion is energized with microwave energy to release and/or activate at least one bioactive material.

In a preferred embodiment, a catheter system for bioactive material delivery to a body tissue being disposed about a lumen, the system comprises an elongate catheter having a proximal end and a distal end with an axis therebetween. The catheter has a radially expandable balloon near the distal end and an energy delivery surface proximate the balloon for transmission of energy. A plurality of biomolecules have a thermally releasable drug portion and an inert portion covalently bound to the balloon. An energy source is operatively coupled to a controller to selectively energize the delivery portion so as to heat the biomolecules to release the bioactive material to the body tissue.

In an exemplary embodiment, a method of delivering a bioactive material in a lumen comprises engaging a body tissue disposed about the lumen with a plurality of biomolecules. A thermally releasable drug portion and an inert portion are covalently bound to the balloon near a distal end of a catheter when the expandable balloon expands. An electrode delivery portion of the catheter proximate the balloon is energized to heat the biomolecules and release the drug portion from the biomolecules into the body tissue in response to the heating of the biomolecules.

In a preferred embodiment, a catheter system for selective fluid delivery to a body tissue being disposed about a lumen comprises an elongated flexible catheter body. The body has a proximal end and a distal end. A radially expandable structure os near the distal end of the catheter body. A plurality of fluid delivery channels expandable with the expandable structure, the fluid delivery channels are initially blocked with a thermally changeable material. An energy source is operatively coupled to the fluid delivery channels to heat and liquefy the thermally changeable material to open one or more of the fluid delivery channels for fluid release.

In another embodiment, the plurality of fluid delivery channels protrude from the expandable structure to penetrate the body tissue of the lumen.

In another embodiment, a tissue analyzer is configured to characterize the body tissue.

In yet another embodiment, the fluid delivery channels can be selectively energized to selectively open one or more fluid delivery channels in response to the characterized body tissue.

In another embodiment, the radially expandable structure comprises a balloon and the fluid delivery channels are mounted on a circumference of the balloon. In yet another embodiment, the radially expandable structure includes an expandable basket and the fluid delivery channels are mounted on a circumference of the basket.

In another embodiment, the body tissue of the lumen includes a diseased portion. Select electrodes are energized to selectively open one or more fluid delivery channels proximate the diseased portion.

In another embodiment, select electrodes are energized to heat the body tissue in conjunction with the release of the fluid in the lumen.

In other embodiments, the fluid is selected from at least one of, ceramide, suramin, rapamycin, paclitaxel, sirolimus, zotarolimus, everolimus, a therapeutic fluid, an anesthetic drug, a therapeutic drug, a small molecule, a gene therapeutic compound, an anti-thrombolytic agent, a lubricant (to allow higher temperatures without sticking), an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

In a preferred embodiment, a catheter system for selective fluid delivery to body tissue is disposed about a lumen. The system includes an elongated flexible catheter body having a proximal end and a distal end. A radially expandable structure is located near the distal end of the catheter body. A plurality of fluid delivery channels are oriented to be urged against the body tissue of the lumen when the expandable structure expands. A plurality of micro-electromechanical systems (MEMS) are coupled to the fluid delivery channels to selectively open one or more fluid delivery channels and release a fluid in the lumen.

In another embodiment, a method for selective fluid delivery in a lumen includes engaging a body tissue disposed about the lumen with a plurality of fluid delivery channels by a radially expanding a structure within the lumen. One or more of the fluid delivery channels are selectively opened and release a fluid from the select fluid delivery channels into the lumen.

In another embodiment, one or more fluid delivery channels include a plurality of micro-electromechanical systems (MEMS) coupled to the fluid delivery channels to selectively open and/or close the fluid delivery channels.

In a preferred embodiment, a catheter assembly for drug delivery to a body tissue disposed about a lumen includes an elongate catheter having a proximal end and a distal end with an axis in between. A radially expandable porous balloon has an inner surface and an outer surface. The balloon is positioned near the distal end of the catheter with an energy delivery surface proximate the balloon for transmission of energy. A selectively porous membrane, having an inner surface and an outer surface, is overlaid on the balloon. An inflation media, including a drug, for inflating the balloon is introduced between the outer surface of the porous balloon and the inner surface of the membrane when the balloon is inflated with the inflation media. An energy source is coupled to the proximal end of the catheter to deliver energy to the energy delivery surface while the balloon is expanded within the lumen to deliver the drug from the outer surface of the balloon through the membrane to the body tissue.

In another embodiment, a catheter system for selective drug delivery to a body tissue being disposed about a lumen includes an elongated flexible catheter body having a proximal end and a distal end. A radially expandable balloon near the distal end of the catheter body has an inner and outer surface. The outer surface is comprised of a biocompatible matrix and a coating of a soluble bioactive material on the matrix. The material is oriented toward a moist surface of the tissue to allow the moisture to solubilize the bioactive material and force it from the matrix when the balloon is expanded against the tissue and a fluid pressure overcomes an osmotic pressure.

In other embodiments, a system for the treatment of a target tissue by directionally delivering energy and/or bioactive material comprising an elongate catheter having a proximal end and a distal end with an axis therebetween. The catheter has a radially expandable balloon near the distal end and an energy delivery surface on the balloon. A changeable coating having a releasable bioactive material is coupled to the balloon. The changeable coating is oriented to be urged against the target tissue when the balloon expands. An energy source operatively coupled to the catheter to energize the energy delivery surface so as to change the changeable coating and release the bioactive material to the target tissue.

In many exemplary embodiments, the balloon portion may further comprise one or more surface coatings or layers containing a bioactive or a plurality of bioactives that are directed to tissue through the application of energy, exposure to the in vivo environment, or a combination thereof.

In some exemplary embodiments, surfaces of the balloon catheter may further comprise lubricant, electrically conductive compound, compound intended to migrate through the layers of tissue to carry energy to the interstitial layers, or any combination thereof.

In other exemplary embodiments, the balloon portion may further comprise insulative portions that preferably avoid the direct transmission of energy to the area most proximate to the electrodes.

In yet other exemplary embodiments, the balloon portion may be comprised of bioactives attached directly to the surface of the balloon.

In yet other exemplary embodiments, the balloon catheter system is further comprised of a means for transmitting light energy that may be used to release bioactives, activate bioactives, or a combination thereof.

In yet other alternate exemplary embodiments, the balloon may be comprised of delivery channels, or porous material, or a matrix, or a combination thereof, that aides in the delivery of bioactives.

Preferred embodiments of the present invention may be used in therapeutic procedures for achieving biologic effects in tissue. Most preferably, the present invention may be used at any point and time before, during, and/or after an angioplasty procedure.

DETAILED DESCRIPTION OF THE INVENTION

Embodiments of the present invention relate to the treatment of targeted tissue by directionally delivering energy and bioactive materials in order to achieve a therapeutic effect. Preferably, the target tissue is luminal tissue, which may further comprise diseased tissue such as that found in arterial disease. However, any tissue may be targeted for therapy comprising directional delivery of energy and/or delivery of bioactive agents. The directional delivery of energy may be used to treat tissue, aid in the delivery of bioactives, aid tissue uptake of bioactives, or any combination thereof.

Bioactives contemplated by the present invention may be delivered alone or in combination. Examples of bioactives may be large or small molecules, and may include, but are not limited to, antiproliferatives, antithrombins, immunosuppressants, lipids, anti-lipids, liposomes, anti-inflammatories, antineoplastics, antiplatelets, angiogenic agents, anti-angiogentic agents, vitamins, aptamers, antimitotics, metalloproteinase inhibitors, NO donors, estradiols, anti-sclerosing agents, vasoactives, growth factors, beta blockers, AZ blockers, hormones, statins, antioxidants, membrane stabilizing agents, calcium antagonists, retinoids, peptides, lipoproteins, polypeptides, polynucleotides encoding polypeptides, proteins, protein drugs, enzymes, genetic material, cells, energy-activated agents, anti-lymphocytes, and anti-macrophage substances.

Figure 7:
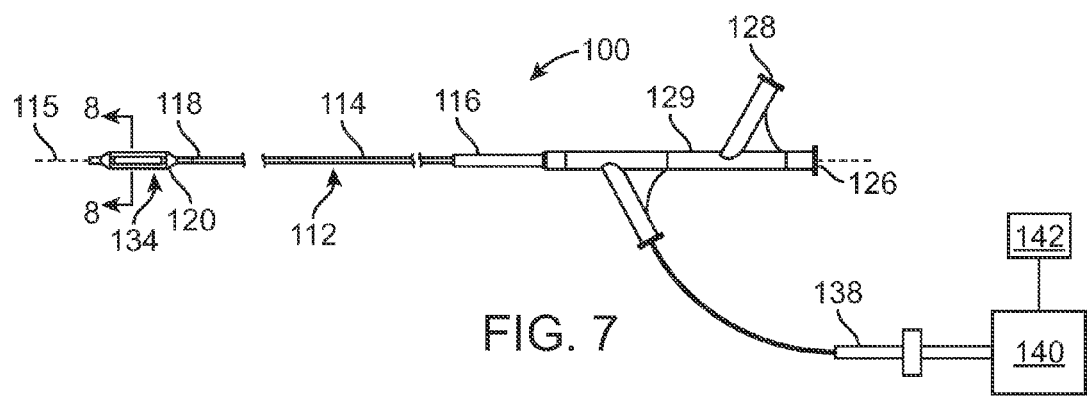
FIG. 7 schematically illustrates another embodiment of a catheter system having fluid delivery channels for selective fluid delivery to a body tissue being disposed about a lumen.

A bioactive may be incorporated into a coating on a balloon catheter that may be released through the directed application of energy once inside the lumen to selectively treat targeted tissue. Some embodiments of the present invention use heating to release the bioactive coating. Other embodiments combine bioactive delivery with heating of the target tissue before, during, and/or after delivery to the tissue. Devices for heating tissue using RF (i.e. radio frequency), ultrasound, microwave and laser energies have been disclosed in U.S. patent application Ser. Nos. 11/975,474, 11/975,383, 11/122, 263 and U.S. Provisional Application No. 61/099,155, the full disclosures of which are incorporated herein by reference. Schematics of balloon catheter based energy delivery systems are shown in FIG. 1 and FIG. 7.

Drug Delivery Coatings

Figure 1:
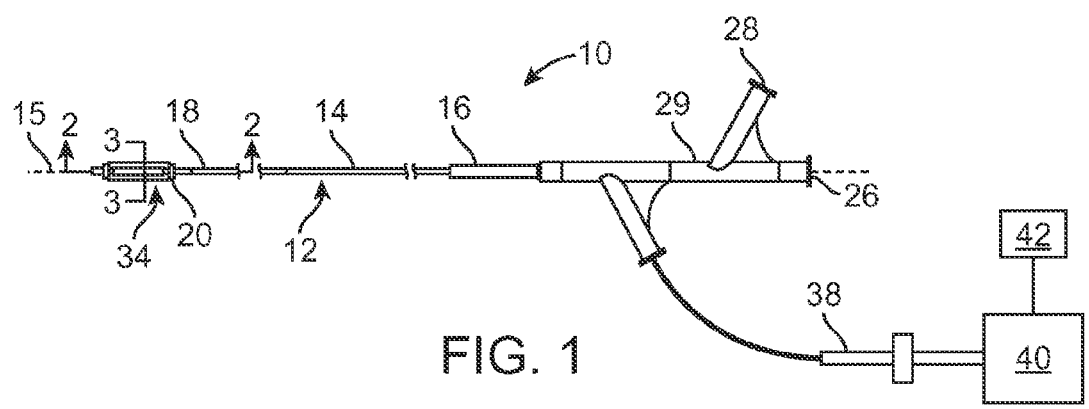
FIG. 1 schematically illustrates one embodiment of a catheter system having a coating for selective bioactive delivery to a body tissue being disposed about a lumen.

FIG. 1 shows one embodiment of a catheter system 10 having a releasable coating for selective drug delivery to a body tissue being disposed about a lumen. The catheter system 10 includes a balloon catheter 12 having a catheter body 14 with a proximal end 16 and a distal end 18. Catheter body 14 is flexible and defines a catheter axis 15, and may include one or more lumens, such as a guidewire lumen 22 and an inflation lumen 24. Catheter 12 includes an inflatable balloon 20 adjacent distal end 18 and a housing 29 adjacent proximal end 16. Housing 29 includes a first connector 26 in communication with guidewire lumen 22 and a second connector 28 in fluid communication with inflation lumen 24. Inflation lumen 24 extends between balloon 20 and second connector 28. Both first and second connectors 26, 28 may optionally comprise a standard connector, such as a Luer-Loc™ connector. A distal tip may include an integral tip valve to allow passage of guidewires, and the like.

Housing 29 also accommodates an electrical connector 38. Connector 38 includes a plurality of electrical connections, each electrically coupled to electrodes 34 via conductors 36. This allows electrodes 34 to be easily energized, the electrodes often being energized by a controller 40 and power source 42, such as RF energy. In one embodiment, electrical connector 38 is coupled to an RF generator via a controller 40, with controller 40 allowing energy to be selectively directed to electrodes 34. While RF energy is disclosed, other suitable energy sources may be used, such as microwave energy, ultrasound energy, or laser energy, each having energy delivery surfaces configured to deliver the desired energy. See copending U.S. Provisional Application No. 61/099,155 filed Sep. 22, 2008 the full disclosures of which are incorporated herein by reference.

In some embodiments, controller 40 may include a processor or be coupled to a processor to control or record treatment. The processor will typically comprise computer hardware and/or software, often including one or more programmable processor unit running machine readable program instructions or code for implementing some or all of one or more of the methods described herein. The code will often be embodied in a tangible media such as a memory (optionally a read only memory, a random access memory, a non-volatile memory, or the like) and/or a recording media (such as a floppy disk, a hard drive, a CD, a DVD, a non-volatile solid-state memory card, or the like). The code and/or associated data and signals may also be transmitted to or from the processor via a network connection (such as a wireless network, an Ethernet, an internet, an intranet, or the like), and some or all of the code may also be transmitted between components of catheter system 10 and within processor via one or more bus, and appropriate standard or proprietary communications cards, connectors, cables, and the like will often be included in the processor. Processor will often be configured to perform the calculations and signal transmission steps described herein at least in part by programming the processor with the software code, which may be written as a single program, a series of separate subroutines or related programs, or the like. The processor may comprise standard or proprietary digital and/or analog signal processing hardware, software, and/or firmware, and will typically have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touch screen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

Figure 2:
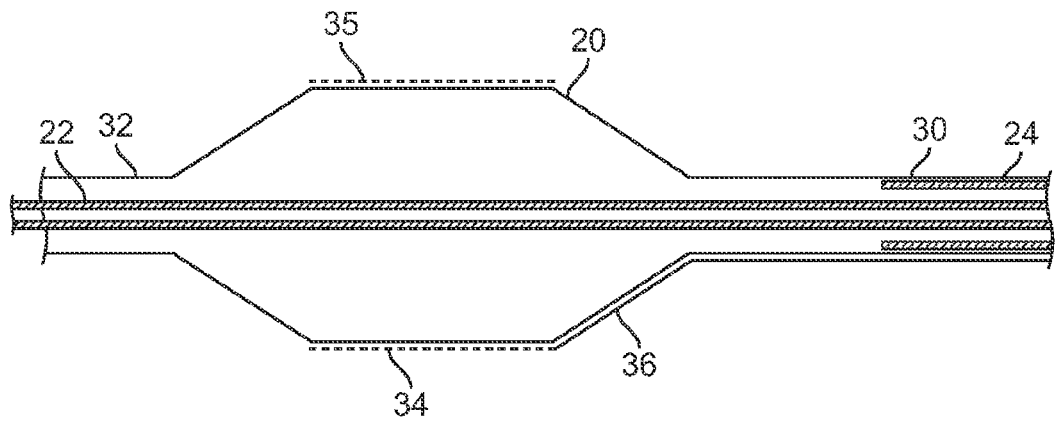
FIG. 2 schematically illustrates one embodiment of an inflatable balloon for use in the catheter system of FIG. 1.

Balloon 20 is illustrated in more detail in FIG. 2. Balloon 20 generally includes a proximal portion 30 coupled to inflation lumen 24 and a distal portion 32 coupled to guidewire lumen 22. Balloon 20 expands radially when inflated with a fluid or a gas. In some embodiments, the fluid or gas may be non-conductive and/or cooled. In some embodiments, balloon 20 may be a low pressure balloon pressurized to contact the artery tissue. In other embodiments, balloon 20 is an angioplasty balloon capable of higher pressure to both heat the artery tissue and expand the artery lumen. Balloon 20 may comprise a compliant or non-compliant balloon having helical folds to facilitate reconfiguring the balloon from a radially expanded, inflated configuration to a low profile configuration, particularly for removal after use.

Electrodes 34 are mounted on a surface of balloon 20, with associated conductors 36 extending proximally from the electrodes. Electrodes 34 may be arranged in many different patterns or arrays on balloon 20. The system may be used for monopolar or bipolar application of energy. For delivery of bipolar energy, adjacent electrodes are axially offset to allow bipolar energy to be directed between adjacent circumferential (axially offset) electrodes. In other embodiments, electrodes may be arranged in bands around the balloon to allow bipolar energy to be directed between adjacent distal and proximal electrodes.

Figure 3A:
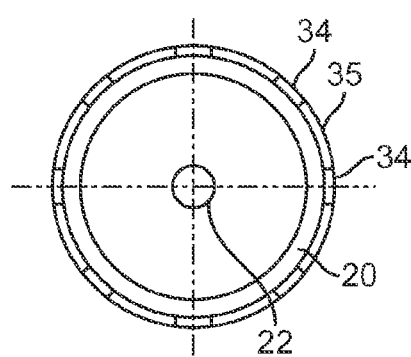
FIG. 3A schematically illustrates a cross-sectional view and 3B is an enlarged view of the balloon of FIG. 2.
Figure 3B:
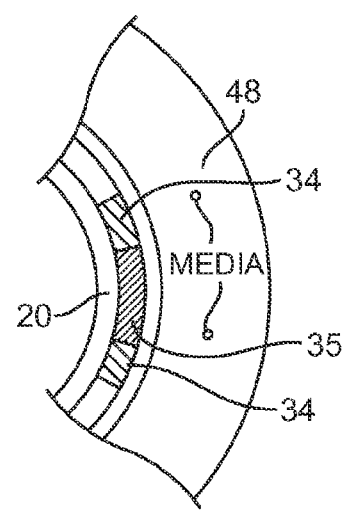
FIG. 3C schematically illustrates a layered coating on the balloon of 3A.

A coating 35 is coupled to the balloon 20 and positioned between electrodes 34, such as shown in FIGS. 3A and 3B. Coating 35 includes a fluid or drug to be delivered to the targeted tissue. It is envisioned that the coating will be thermally activated and configured to be released from the balloon surface at a temperature above body temperature (greater than 37 C). The idea is to have the energy delivery or heat, change the phase of a coating compound from a solid to a liquid, and releases the drug. This temperature increase involves activating electrodes 34 using RF energy. As the energy is increased, the coating 35 between the electrodes 34 is heated and released thermally to the local tissue 48. Coating 35 is durable or flexible such that it can be folded with the balloon 20 without separation or delamination. This mechanism could release small or large molecular drug or pharma product. The drug could be in a solid gel form.

Figure 3C:
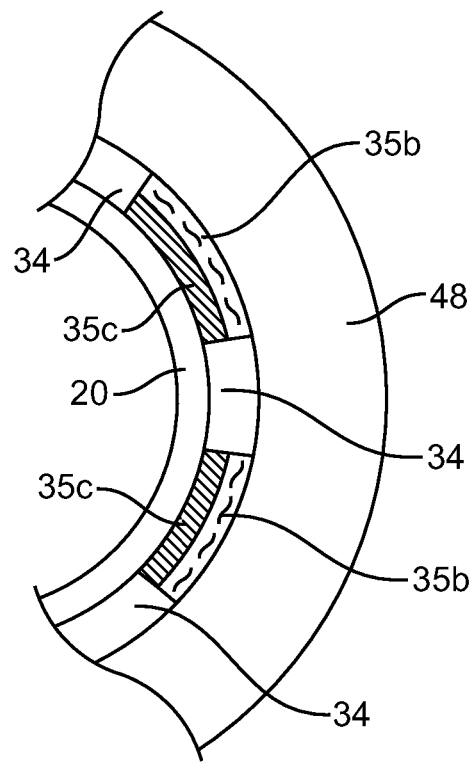

In some embodiments, the layer of coating 35b on the balloon 20 may incorporate more than one bioactive, fluid, or coating layer (FIG. 3C), each having different physical properties, such as phase change temperatures. For example, an anesthetic could be administered at a lower melting temperature prior to a specific treatment of higher temperature where there may be a nerve in the general location. In some embodiments, as shown in FIG. 3C, coatings of differing material may be used, such as by layering. For example, a first layer may include a first bioactive 35b that attaches to the target tissue 48 acting as a receptor to a second bioactive 35c in a second layer.

Figure 4A:
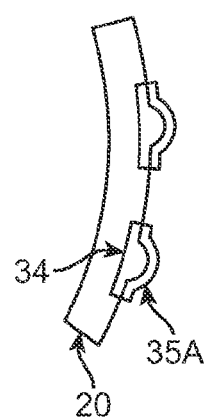
FIGS. 4A and 4B schematically illustrate coatings covering the electrodes.

In some embodiments, a second coating 35A may be used to cover electrodes 34, such as shown in FIG. 4A. Second coating 35A may be an insulating coating on the electrodes 34. The second coating 35A would be used when treating inside a metallic object in the lumen, such as a stent, because if the electrodes 34 come in contact with metal, they may short circuit thus ending the treatment, for example. If the electrodes 34 are coated with a material with electrical properties such that the electrodes can not be shorted with metallic objects, the treatment can continue even when in contact with metal objects. This would allow catheter system 10 to treat inside objects like stents. Second coating 35A may also act to insulate electrodes 34 from tissue 48, shown in FIG. 4B, which stops/prohibits energy flow through tissue 48 and sends the energy through coating 35, heating only the coating 35 between the electrodes 34, releasing the drug to the tissue 48. The second coating 35A may also include a different drug than coating 35.

Figure 4B:
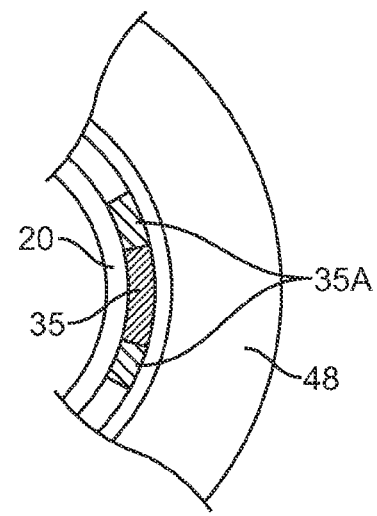
Figure 4C:
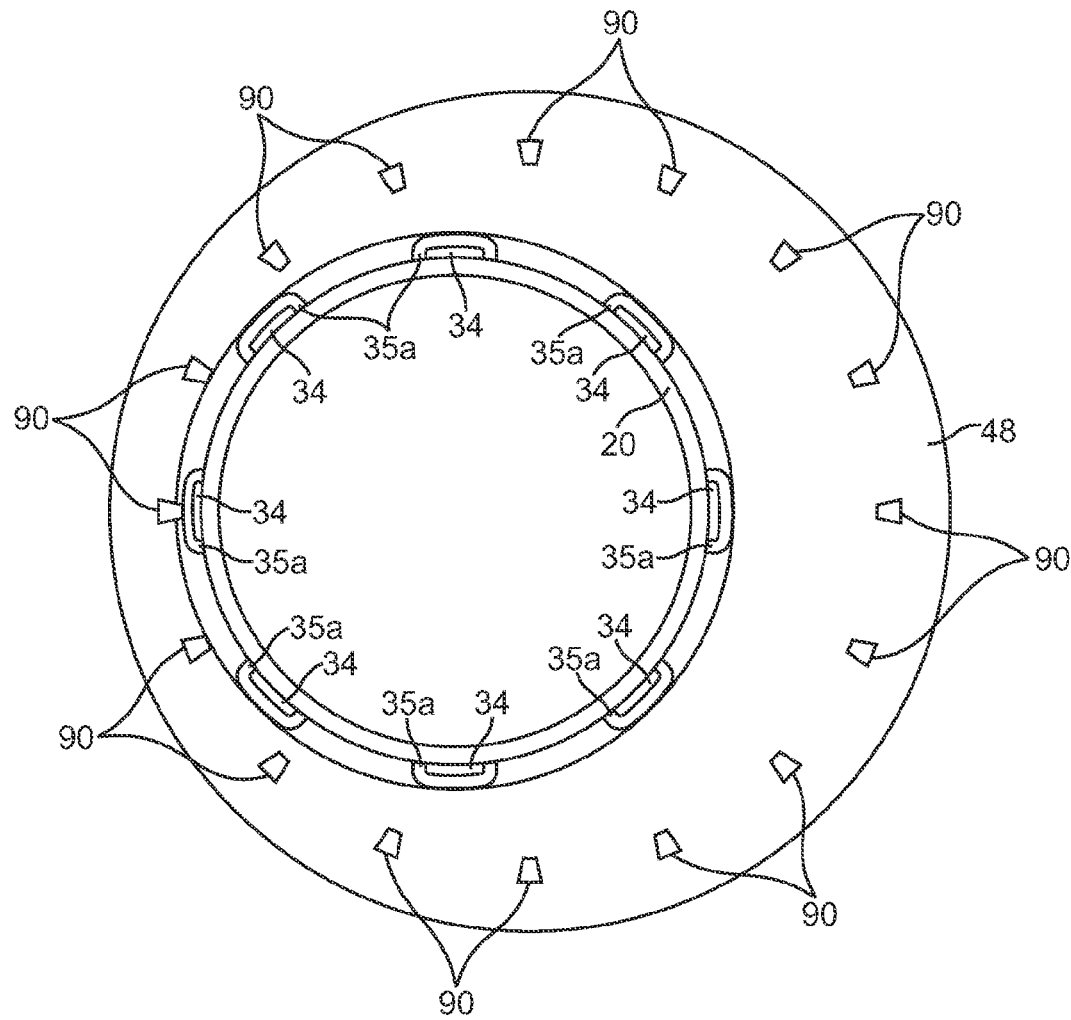
FIG. 4C schematically illustrates covered electrodes being used to treat tissue.

To illustrate, as shown in FIG. 4C, the insulating coating is preferably used when treating inside or near a metallic object located inside of a lumen, such as a stent where in-stent restenosis 90 is present, because if the electrodes come into contact with metal, they may short circuit and the treatment will end. Therefore, in some embodiments it is preferable for the electrodes to be insulated to avoid short circuit when in proximity with conductive objects such as metals (FIG. 4C), thereby allowing that treatment may continue in such circumstances. The insulating coating may also act to insulate electrodes from tissue, which may cause energy to be directed to selected locations on the balloon while preventing energy from flowing directly to tissue sites.

Many types of drugs may be included in the coatings. For example, the coating may include drugs currently used in drug eluting stents, such as sirolimus (used in the Cypher™ stent), paclitaxel (used in the Taxus™ stent), zotarolimus (used in the Endeavour™ stent) and everolimus (used in the Xience V™ stent).

Some embodiments of the present invention may include aptamers 52 coated to the balloon 20 using a substrate that breaks down readily when heated, such as when the RF energy source is activated. Aptamers are oligonucleic acid or peptide molecules that bind to a specific target molecule. They can be engineered to bind very specifically to various molecular targets such as small molecules, proteins, nucleic acids, and even cells, tissues and organisms. The aptamers 52 could be synthesized to bind 54 with desired tissue 48 to be treated, such as plaque, within the lumen or artery.

Figure 5:
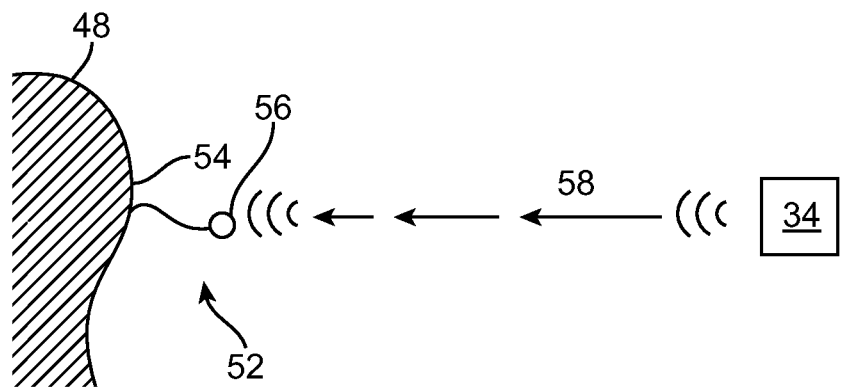
FIG. 5 schematically illustrates the used of aptamers in treating tissue.

While the catheter system 10 is not powered and the balloon 20 deflated, the coating 35 with aptamers 52 would remain on the balloon 20. Once the balloon 20 is inflated and the energy unit turned on, the coating is released and the aptamers 52 bind to the desired tissue, such as shown in FIG. 5. In some embodiments, aptamers 52 would be conjugated to a microscopic bead 56 that is highly receptive to the energy 58, such as RF energy, emitted by the catheter system 10. The beads 56 convert the RF energy to thermal energy directly and only to the tissue that the aptamers 52 is in contact with.

Aptamers are nucleic acids that bind to the surface of molecules in much the same way as antibodies. One importance difference between aptamers and antibodies is that aptamers can be produced by chemical synthesis whereas antibodies are produced biologically, first animals, then in culture or an expression system. Another important difference is that aptamers are very stable and not sensitive to their surrounding environment, including temperature.

In some embodiments, coating 35 may include a chemical solvent that has plaque softening properties. Ether, chloroform, benzene, and acetone are known to be lipid solvents. Furthermore, amino acids, proteins, carbohydrates, and nucleic acids are largely insoluble in these solvents. If the solvent is used in conjunction with tissue heating, the tissue treatment may require less energy over a shorter time period, lessening the chance of damage to healthy tissue. If the tissue includes calcium deposits, the same process used to deliver lipid solvents to plaque could be used to deliver calcium solvents to calcification sites. Calcium is highly soluble in a variety of organic solvents. In both cases, the solvent would be coupled to the surface of the balloon with a coating that would break down either with the application of heat or RF energy, or as the balloon is inflated.

In some embodiments, the coating may incorporate more than one drug, agent, or fluid listed herein within the coating, each having different phase change temperatures. For example, an anesthetic could be administered at a lower melting temperature prior to a specific treatment of higher temperature where there may be a nerve in the general location. Is some embodiments, two coatings of differing material may be used, such as by layering. For example, a first layer may include a first drug that attaches to the target tissue and act as a receptor to a second drug in a second layer. In some embodiments the coating is non-conductive to reduce or eliminate electrical shorts between electrodes.

In some embodiments, tissue signature could be used to identify treatment regions with the use of impedance measurements. Impedance measurements utilizing the radially spaced electrodes 34 within a lumen can be used to analyze tissue. Impedance measurements between pairs of adjacent electrodes (and/or between pairs of separated electrodes), may differ when the current path passes through diseased tissue, and when it passes through healthy tissues of the luminal wall. Hence, impedance measurements between the electrodes on either side of diseased tissue may indicate a lesion, while measurements between other pairs of adjacent electrodes indicate healthy tissue. Other characterization, such as intravascular ultrasound, optical coherence tomography, or the like may be used to identify regions to be treated.

Some embodiments described herein may be used to treat atherosclerotic disease by selective drug delivery in combination with "gentle heating" utilizing the "Q10 Rule" to further enhance the fluid or drug treatment. Under the Q10 Rule, it is well known that rates of biochemical reactions usually double when temperature is increased by 10° C.

Figure 6:
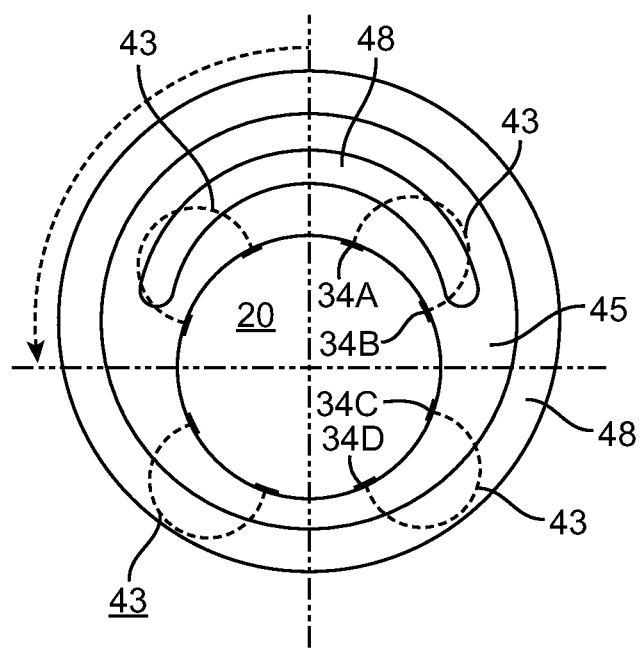
FIG. 6 schematically illustrates placement of electrode pairs for use in tissue analysis and selective energy treatment before, during, and/or after bioactive delivery.

As shown in FIG. 6, electrodes 34 are positioned circumferentially around the balloon 20. RF energy 43 is directed to electrodes adjacent pairs of electrodes 34A and 34C, or 34A and 34D, or any combination of 34A-34D, treating both the healthy tissue 45 and atherosclerotic material 48 within lumen 50. This arrangement creates an energy path 43 through the tissue that delivers energy or heat ("tissue remodeling energy") in particular treatment zones or segments to the artery tissue between the electrode pairs ("remodeling zones") having a volume between the electrode pairs at a specific depth. Using different combinations of electrode pairs may reduce or eliminate gaps between the remodeling zones by using overlapping pairs. Using electrode pairs with bipolar energy may avoid some potential issues of the monopolar approach. Diseased artery tissue 48 has a higher electrical resistivity than healthy artery tissue. By using pairs of electrodes 34A, 34B in a bipolar system, tissue remodeling energy will go through the healthy tissue, diseased tissue, or a combination of both healthy and diseased tissues between the electrode pairs in the remodeling zones. Any number of electrode pairs may be used in different patterns or arrays to create a number of remodeling zones. The controller may apply either constant power, constant current, or constant voltage, whichever has the most advantage.

The controller 40 may energize the electrodes with about 0.25 to 5 Watts average power for 1 to 180 seconds, or with about 4 to 45 Joules. Higher energy treatments are done at lower powers and longer durations, such as 0.5 Watts for 90 seconds or 0.25 Watts for 180 seconds. Most treatments in the 2 to 4 Watt range are performed in 1 to 4 seconds. Using a wider electrode spacing, it would be appropriate to scale up the power and duration of the treatment, in which case the average power could be higher than 5 Watts, and the total energy could exceed 45 Joules. Likewise, using a shorter or smaller electrode pair would require scaling the average power down, and the total energy could be less than 4 Joules. The power and duration are calibrated to be less than enough to cause severe damage, and particularly less than enough to ablate diseased tissue 48 within a blood vessel.

In some embodiments the delivery of the drug and gentle heat may be accompanied by balloon angioplasty using gentle dilation to remodel the artery with dilation pressures which are at or significantly lower than standard, unheated angioplasty dilation pressures. Where balloon inflation pressures of 10-16 atmospheres may, for example, be appropriate for standard angioplasty dilation of a particular lesion, modified dilation treatments combined with appropriate electrical potentials (through flexible circuit electrodes on the balloon, electrodes deposited directly on the balloon structure, or the like) described herein may employ from 10-16 atmospheres or may be effected with pressures of 6 atmospheres or less, and possibly as low as 1 to 2 atmospheres. Such moderate dilations pressures may (or may not) be combined with one or more aspects of the tissue characterization, tuned energy, eccentric treatments, and other treatment aspects described herein for treatment of diseases of the peripheral vasculature.

Covalently Bound BioMolecules

Current endovascular therapies for preventing or permanently removing hyperplastic neointima are not completely efficacious. While removal of such tissue is achieved by multiple such therapies, regrowth of the tissue is a frequent occurrence, leading to restenosis and dysfunctional blood flow. Drug-eluting stents are able to inhibit the frequency of restenosis, but fall short of completely restoring vascular function, owing to the presence of a persistent implant; the stent.

More recently, drug clotting balloons have shown an even greater reduction in the frequency of restenosis than drug eluting stents and are removed after treatment, however, high pressure inflation is required to optimally deliver the anti-proliferation/anti-inflammatory biomolecules. The molecules may function to prevent restenosis by preventing inflammatory cell influx (chemo taxis), cell proliferation. The molecules may also function to stabilize the IEL matrix by providing structural support, thus "setting" the lumen diameter.

Figure 9A:
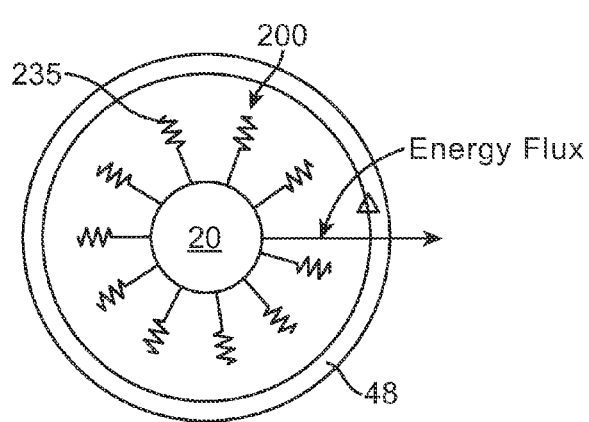
FIGS. 9A and 9B schematically illustrate cross-sectional views showing tissue treatment using bioactive molecules having a thermally releasable active portion and an inert portion coupled by bond to a balloon surface.
Figure 9B:
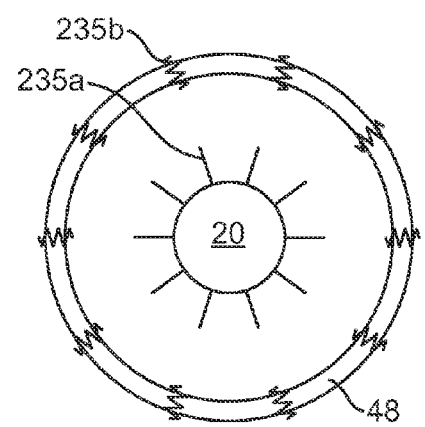

Moving now to FIGS. 9A and 9B, another embodiment of a catheter system 200 for drug delivery to a body tissue 248 is depicted. The system 200 is similar to system 10 above, except the use of biomolecules 235 coupled to the balloon 20 instead of a coating. The biomolecules 235 include a thermally releasable active portion 235$a$ and an inert portion 235$b$ coupled by covalent bond to a balloon 20 surface. The active portion or molecule 235$b$ is capable of treating the desired tissue 248, which may be enhanced with temperature or pressure. The inert portion 235$a$ of the biomolecule stays on the balloon. The embodiment described herein utilizes a radiofrequency endovascular balloon catheter that, upon low pressure inflation and energy delivery from the balloon to the atherosclerotic lesion, hyper-thermally releases the active portion of the biomolecule that is covalently bound to the balloon, thus, delivering the active portion of the molecule to the targeted tissue. The energy may also include ultrasound emitting energy. The active molecule 235$b$ functions to prevent production of hyperplastic tissue by any means, including, but not limited to, cytostasis (prevention of mitosis), receptor maturation (i.e., those receptors at/on cells on the targeted tissue that are adhesive to/for a chemotactic to/for infiltrating cells that promote hyperplastic tissue formation.

The molecule's bioactive portion 235$b$ is released from the intact biomolecule 235 by delivery of energy (such as from electrodes 34) that induces a local hyperthermia environment. The molecule is stable under the hyperthermia conditions. The molecule can prevent one or all of the following functions: 1) cell proliferation; 2) cell function; 3) receptor-ligand binding; 4) chemotaxis of inflammatory cells to the target tissue; and 5) migration of cells in the native artery strata to the diseased tissue.

The influx of the molecule 235$b$ into the diseased tissue 48 is facilitated and/or hastened by the energy mediated hypothermia, i.e., cleavage from the intact biomolecule, migration into the diseased tissue, and residence in the diseased tissue by virtue of increased porosity are all accelerated by the hyperthermia. This invention uniquely delivers a bioactive molecule into diseased tissue with: 1) greater speed by hypothermal acceleration; 2) more completeness by rendering the diseased tissue more receptive/porous to the molecule; and/or 3) no inactive segments of the biomolecule (i.e., no polymer, inactive protein sequence/segment, or co-factors required for activation left at the treatment site since the inactive segments stay on the balloon).

Clinical application and uses are designed to reduce plaque, inhibit restenosis in stented or not-stented site, and may be used as an adjunctive treatment to aggressive non-implantable endovascular procedures and stent implants.

Fluid Delivery Channels

FIG. 7 shows another embodiment of a catheter system 100 having fluid delivery channels for selective fluid delivery to a body tissue being disposed about a lumen. The catheter system 100 includes a balloon catheter 112 having a catheter body 114 with a proximal end 116 and a distal end 118. Catheter body 114 is flexible and defines a catheter axis 115, and may include one or more lumens, such as a guidewire lumen 122 and an inflation lumen 124. Catheter 112 includes an inflatable balloon 120 adjacent distal end 118 and a housing 129 adjacent proximal end 116. Housing 129 includes a first connector 126 in communication with guidewire lumen 122 and a second connector 128 in fluid communication with inflation lumen 124. Inflation lumen 124 extends between balloon 120 and second connector 128. Both first and second connectors 126, 128 may optionally comprise a standard connector, such as a Luer-Loc™ connector. A distal tip may include an integral tip valve to allow passage of guidewires, and the like.

Housing 129 also accommodates an electrical connector 138. Connector 138 includes a plurality of electrical connections, each electrically coupled to electrodes 134 via conductors 136. This allows electrodes 134 to be easily energized, the electrodes often being energized by a controller 140 and power source 142, such as RF energy, microwave energy, ultrasound energy, or other suitable energy sources. In one embodiment, electrical connector 138 is coupled to an RF generator via a controller 140, with controller 140 allowing energy to be selectively directed to electrodes 134 or electrode pairs. Controller 140 may include a processor or be coupled to a processor to control or record treatment.

Figure 8A:
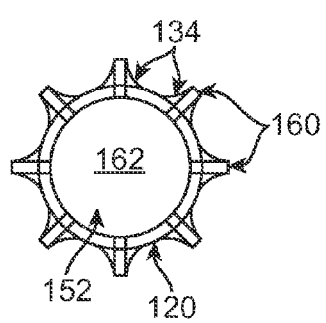
FIG. 8A schematically illustrates a cross-section and FIG. 8B is an enlarged section of the balloon in FIG. 7 showing fluid delivery channels through the balloon coupled to electrodes mounted on a surface of the balloon.
Figure 8B:
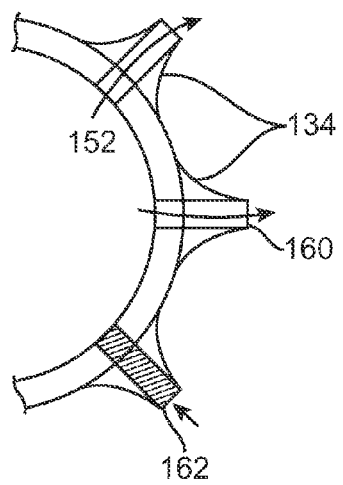

FIG. 8A shows a cross-section of the balloon 120 and FIG. 8B is an enlarged section showing fluid delivery channels 160 through the balloon 120 coupled to electrodes 134 mounted on a surface of balloon 120. Electrodes 134 include associated conductors extending proximally from the electrodes. Electrodes 134 and fluid delivery channels 160 may be arranged in many different patterns or arrays on balloon 120. Fluid delivery channels 160 may be coupled to a fluid reservoir or lumen 162 holding the fluid 152. In some embodiments, the inflation medium may contain the fluid to be delivered. In some embodiments, the channels 160 thru balloon 120 may be filled with wax-like material 164 that can be expelled thermally in order to open the channel (or any other material that can be expelled). In other embodiments, electrodes 134 may open and close a flap to release the fluid.

The delivery channels 160 may protrude from the balloon surface such that they are capable of penetrating the body tissue of the lumen. In some embodiments, the electrodes may penetrate the body tissue.

The catheter system 100 may also include a tissue analyzer configured to characterize the body tissue. In some embodiments, electrodes 134 may be sensing electrodes, as discussed above, that could help characterize the tissue to identify regions the be treated or not using electrical impedance tomography. Other characterization, such as intravascular ultrasound, optical coherence tomography, or the like may be used to identify regions to be treated. Electrodes 134 may be energized in response to the characterized body tissue Some embodiments described herein may be used to treat atherosclerotic disease by selective fluid delivery in combination with "gentle heating" to further enhance the fluid delivery or treatment, as discussed above.

Electrodes 134 may be selectively energized to open or close fluid delivery channels 160 to treat tissue. One method includes opening the fluid delivery channels 160 by selectively heating the electrodes (by Joule heating or other means, including inducing a heightened temperature in the adjacent region, whereby hear transfer could heat the electrode(s)), such that a material 164, that would otherwise block the channel, is phase changed from solid to liquid. Another possible method may include the use of MEMS (micro-elector-mechanical-systems) to open and/or close channels 160 selectively.

In some embodiments, the fluid delivery channels may be vias through the electrodes (perfused electrodes). The vias or small holes may be used to deliver a fluid to the artery tissue proximate the electrode. The holes may be less than 1 μm in diameter and may be made with a laser or ion beam. The holes may be made in the electrodes and balloon. In one example, electrode pads on a flexible circuit are designed with vias that are plated. The flexible circuit is mounted on a balloon and a laser or ion beam is used to create the holes in the flexible substrate and balloon. There may be several holes in the flexible/balloon for every electrode pad. The balloon may then be perfused with standard perfusion balloon equipment or specialized equipment. This perfusion approach may also provide additional advantages beyond fluid delivery, such as eliminating sticking, carry away heat or regulate the impedance of the load.

In some embodiments, a porous balloon may be used having fluid delivery channels on a micro-level, allowing select molecules through with the addition of heat. The porous balloon may have an inner layer, a porous outer layer or membrane, drug or fluid molecules positioned between the layers (i.e., a reservoir) and electrodes coupled to the outer layer. At low pressures, the molecules stay within the reservoir. As heat is applied, the molecules may go through the porous layer, which may be done in different ways. For example, as the heat is applied, the drug molecules may become exited, providing enough force to go through the porous outer layer. In another example, as heat is applied to the balloon, the pores expand, allowing the drug molecules to go through the porous outer layer. The molecules may also pass through the porous outer layer or membrane by osmotic pressure along with the heat.

In some embodiments, the treatments may include a drug, and/or thermal, and/or small or large molecules injection, and/or RF, and/or balloon dilatation, and/or hyperthermia.

Figure 8C:
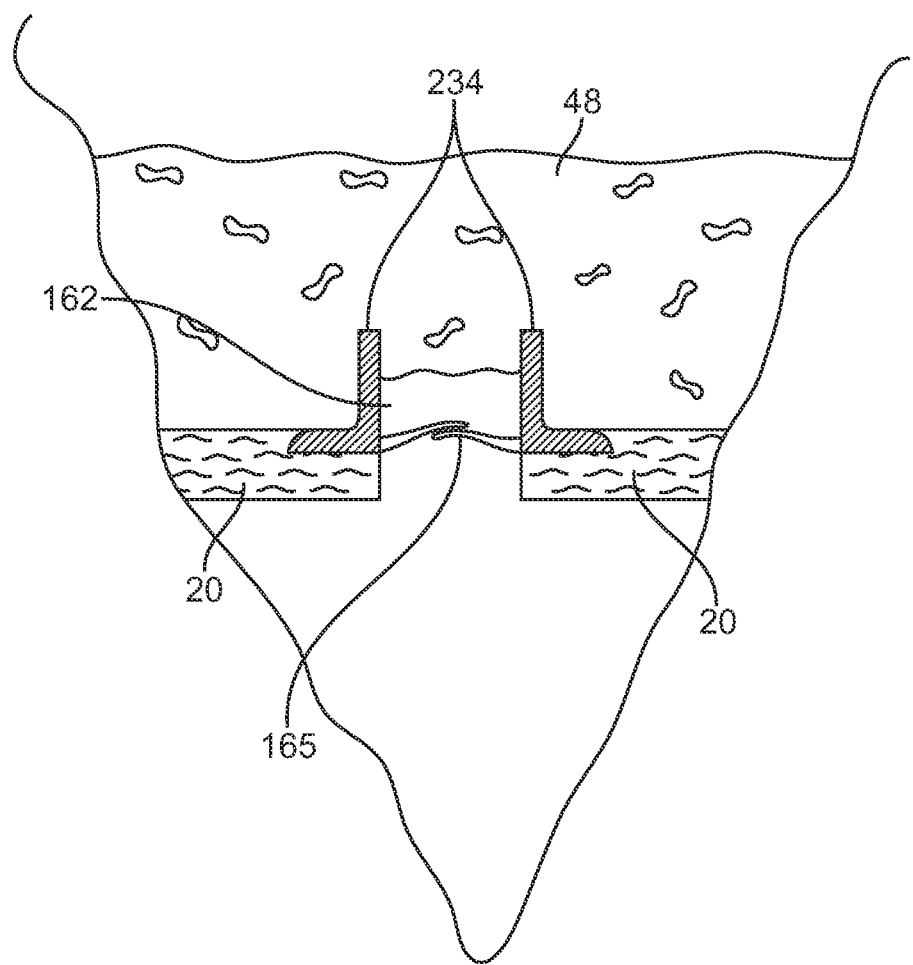
FIG. 8C is an enlarged cross-sectional view showing the fluid delivery channels and electrodes of FIGS. 8A and 8B imbedded into tissue.

In other embodiments, electromechanical or mechanical means known in the art may be employed to release the fluid, which by way of example may include flaps or microfluidic-type devices 165 powered by the controller. As shown in FIG. 8C, the delivery channels 234 may protrude from the balloon surface such that they are capable of penetrating body tissue 48, for example, luminal tissue.

While the devices, systems, and methods disclosed herein discuss a balloon as the radially expandable structure, other expandable structures may also be used, such as described in U.S. patent application Ser. No. 11/975,651 filed Oct. 18, 2007; the full disclosure of which is incorporated herein by reference.

Thermally Excited Osmolarity

In some embodiments, a porous balloon may be used having fluid delivery channels on a micro-level in a membrane, allowing molecules through with the addition of pressure and heat. The concept delivers a fluid or drug to a specific site by passing it through the membrane, much like reverse osmosis. In reverse osmosis, a pressure is used to drive a liquid, such as water, through a membrane with passages so small that only the appropriate molecules can pass through. In this embodiment, the membrane barrier retains a drug, like paclitaxel. At low pressures, the drug molecules are not able to pass through the membrane. To release the drug through the membrane, pressure is applied to the drug molecules using a balloon the release of the drug is the accelerated by applying energy locally by an electrode pair or monopolar electrode.

In many embodiments, an energy delivery surface comprises a plurality of spaced electrodes, such as that shown in FIGS. 3A, 3B, 3C, 4A, 4B, 6, 8A, 8B, 10A, 10B, 11C, 12, 13A, 13B, 13C, 13D, and 14B. An energy source as shown in FIG. 1 and FIG. 7 is operatively coupled to the plurality of electrodes so as to selectively energize selected electrodes. The energy may heat portions of a changeable coating, with the heated portions optionally being between electrodes, to release a bioactive 50 directly or indirectly to the target tissue as shown in FIGS. 3B, 3C, 4B, 5, 9A, 9B, 10A, 10B, 11C, 12, 13C, 14A, and 14B. In many embodiments the tissue may comprise a diseased portion of a lumen and select electrodes are energized to selectively heat a thermally changeable coating proximate the diseased portion.

In many embodiments, the energy delivery surface comprises a plurality of electrodes disposed about an expandable balloon so as to define a plurality of remodeling zones in the target tissue when the balloon is expanded within the lumen. As shown in FIG. 6, the electrodes are preferably coupled with the tissue, and energy may be transmitted between the electrodes and the tissue so as to initiate a biological response. The balloon will typically comprise a distal end of a balloon catheter, and the energy delivery surfaces on the balloon will generally be energized using an energy source coupled to a proximal end of the catheter. An energy conduit may extend along a catheter body between the proximal end and the balloon, with the energy conduit often comprising an electrical conductor (for applying RF energy or the like), a light conductor (such as a fiber optic filament running along a lumen in the catheter body so as to conduct laser or other light energies), or the like.

In some embodiments, tissue signature may be used to identify tissue treatment regions with the use of impedance measurements. Impedance measurements utilizing circumferentially spaced electrodes within a lumen, such as those shown in FIG. 6, may be used to analyze tissue. Impedance measurements between pairs of adjacent electrodes (and/or between pairs of separated electrodes) may differ when the current path passes through diseased tissue, and when it passes through healthy tissues of the luminal wall. Hence, impedance measurements between the electrodes on either side of diseased tissue may indicate a lesion, while measurements between other pairs of adjacent electrodes may indicate healthy tissue. Other characterization, such as intravascular ultrasound, optical coherence tomography, or the like may be used to identify regions to be treated.

Some embodiments described herein may be used to treat atherosclerotic disease by selective delivery of bioactives in combination with "gentle heating" utilizing the "Q10 Rule" to further enhance the bioactive treatment. Under the Q10 Rule, rates of biochemical reactions usually double when temperature is increased by 10 degrees Celsius.

In some embodiments electrodes are separated circumferentially around the balloon and RF energy may be directed to selected electrodes or any selected combination of electrodes. By selecting electrodes to receive energy, a controller such as that shown in FIG. 1 and FIG. 7 may directionally apply energy toward a diseased tissue site for the purpose of applying energy to the tissue (FIG. 6), to release a bioactive (FIGS. 3B, 3C, 4B, 5, 8B, 9B, 10B, 11C, 12, 13C, 14B), to aid in the tissue uptake of a bioactive, or any combination thereof.

In some embodiments, coatings on the balloon or other catheter system surfaces may also be comprised of polymer or polymers (FIGS. 3A, 3B, 3C, 4B, 10A, 10B, 12, 13A, 13B, 14A, 14B), lubricant (for example, to allow higher temperatures without sticking), an electrically conductive compound to lower the impedance at the electrode, an electrically insulating compound to prevent treatment to tissue that does not need treatment (FIG. 4A), an electrically conductive compound that is intended to migrate through the endothelial layers of tissue to carry energy to the interstitial layers (FIG. 5), or any combination thereof.

In embodiments comprising a balloon, the balloon may be further comprised of compliant or non-compliant materials, including combinations thereof, as is well-known in the art.

Tissue Sensing and Selective Direction of Energy

In selectively directing energy, a tissue signature may be used to identify tissue treatment regions with the use of impedance measurements, which may be made by utilizing spaced electrodes, for example, circumferentially spaced electrodes within a lumen as shown in FIG. 6, to perform analysis. Impedance measurements between pairs of adjacent electrodes (and/or between pairs of separated electrodes) may differ when a current path passes through diseased tissue compared to when it passes through healthy tissues, such as those of the luminal wall. Hence, impedance measurements between the electrodes on either side of diseased tissue may indicate a lesion, while measurements between other pairs of adjacent electrodes may indicate healthy tissue. Other characterization, such as intravascular ultrasound, optical coherence tomography, or the like may be used to identify regions to be treated.

In some embodiments, a controller such as that shown in FIG. 1 and FIG. 7 may include a processor or be coupled to a processor to control or record treatment. The processor will typically comprise computer hardware and/or software, often including one or more programmable processor units running machine readable program instructions or code for implementing some or all of one or more of the embodiments and methods described herein. The code will often be embodied in a tangible media such as a memory (optionally a read only memory, a random access memory, a non-volatile memory, or the like) and/or a recording media (such as a floppy disk, a hard drive, a CD, a DVD, a non-volatile solid-state memory card, or the like). The code and/or associated data and signals may also be transmitted to or from the processor via a network connection (such as a wireless network, an Ethernet, an internet, an intranet, or the like), and some or all of the code may also be transmitted between components of a catheter system and within the processor via one or more bus, and appropriate standard or proprietary communications cards, connectors, cables, and the like will often be included in the processor. The processor will often be configured to perform the calculations and signal transmission steps described herein at least in part by programming the processor with the software code, which may be written as a single program, a series of separate subroutines or related programs, or the like. The processor may comprise standard or proprietary digital and/or analog signal processing hardware, software, and/or firmware, and will typically have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touch screen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

The controller may be employed to selectively energize the electrodes with about 0.25 to 5 Watts average power for 1 to 180 seconds, or with about 4 to 45 Joules. Higher energy treatments are done at lower powers and longer durations, such as 0.5 Watts for 90 seconds or 0.25 Watts for 180 seconds. Most treatments in the 2 to 4 Watt range are performed in 1 to 4 seconds. Using a wider electrode spacing, it would be appropriate to scale up the power and duration of the treatment, in which case the average power could be higher than 5 Watts, and the total energy could exceed 45 Joules. Likewise, using a shorter or smaller electrode pair would benefit from scaling the average power down, and the total energy could be less than 4 Joules. The power and duration are calibrated to be less than enough to cause severe damage, and particularly less than enough to ablate diseased tissue within a blood vessel.

Moreover, the Q10 Rule provides for the possibility of combining the release and tissue uptake of bioactives with the directional delivery of energy toward diseased tissue.

Selective Delivery of Energy and Bioactives to Target Tissue

In a preferred embodiment, the balloon portion (FIG. 2) of a balloon catheter is comprised to include a plurality of circumferentially spaced electrodes (FIGS. 3A, 3B, 3C, 4A, 4B, 4C, 6, 8A, 8B, 10A, 10B, 11C, 12, 13A, 13B, 13C, 13D, 14A, 14B). Between the electrodes, a composition comprised of a plurality of bioactives is present on at least a portion of the surface of the balloon (FIGS. 3A, 3B, 3C, 4B, 9A, 10A, 10B, 11C, 12, 13B, 13C, 14A, 14B). The composition containing the plurality of bioactives may be further comprised of other materials such as polymers, gels, lubricant, electrically conductive or non-conductive materials, and the like. Balloon coatings may be applied using dipping, spraying, vapor deposition, and the like. For example, a bioactive may be carried in a balloon coating comprised of a polymer matrix that is stable in human blood at about 37 degrees Celsius, which upon application of energy to selected electrodes causes the balloon coating adjacent to the selected electrodes to locally heat and release constituents of its composition.

Figure 10A:
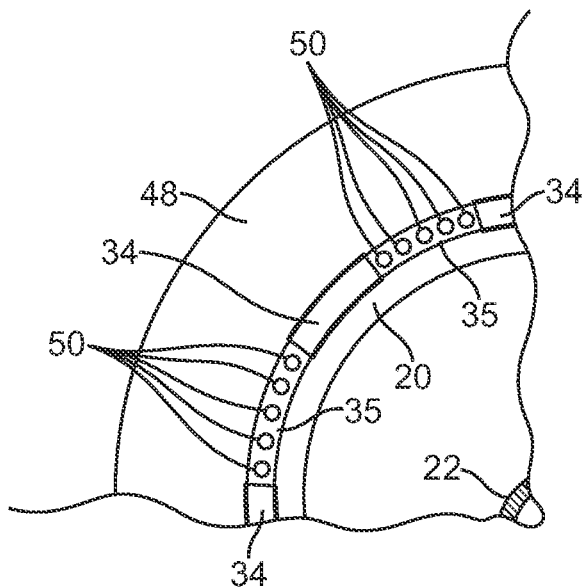
FIGS. 10A and 10B schematically illustrate bioactives on a surface of a balloon being released to targeted tissue.
Figure 10B:
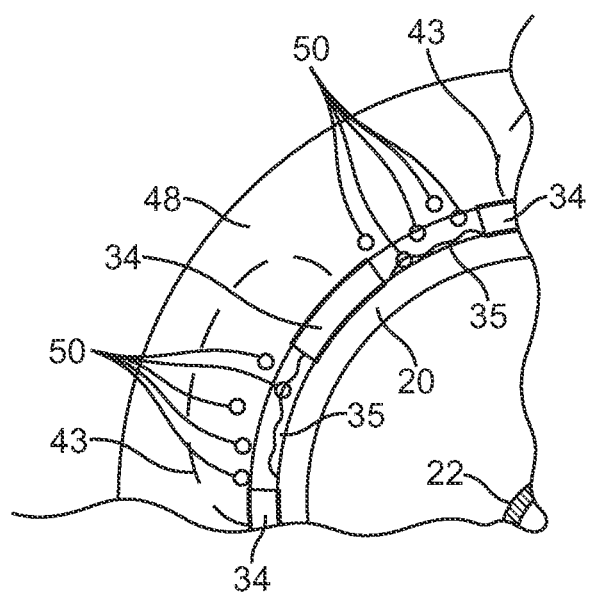
Figure 11A:
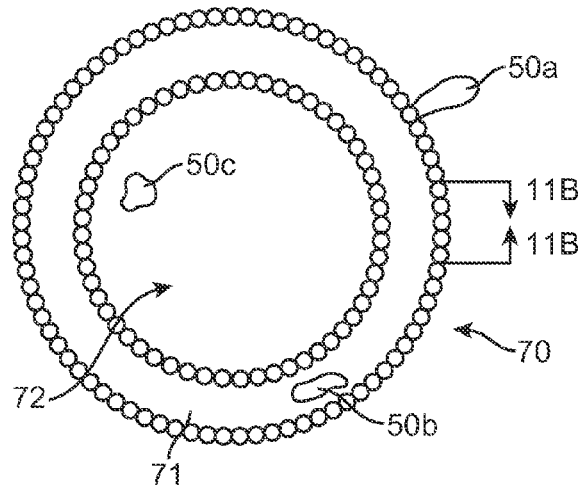
FIG. 11A schematically illustrates a liposome with a plurality of bioactives.
Figure 11B:
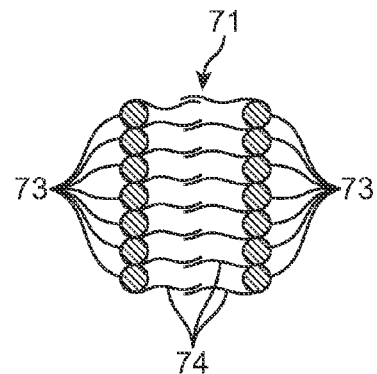
FIG. 11B is an enlarged cross-sectional view of phospholipid bilayer.
Figure 11C:
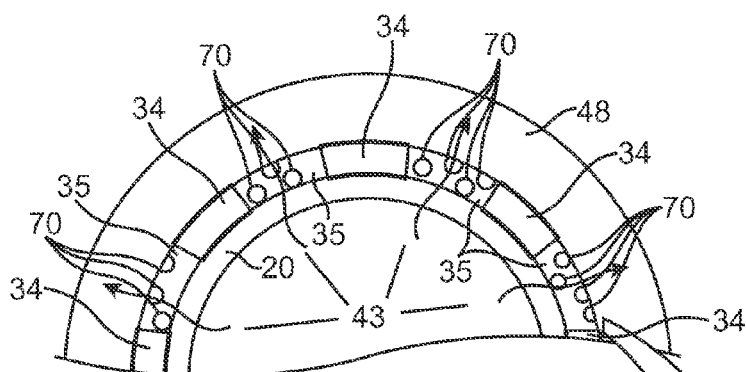
FIG. 11C schematically illustrates the release of liposomes from a balloon.
Figure 12:
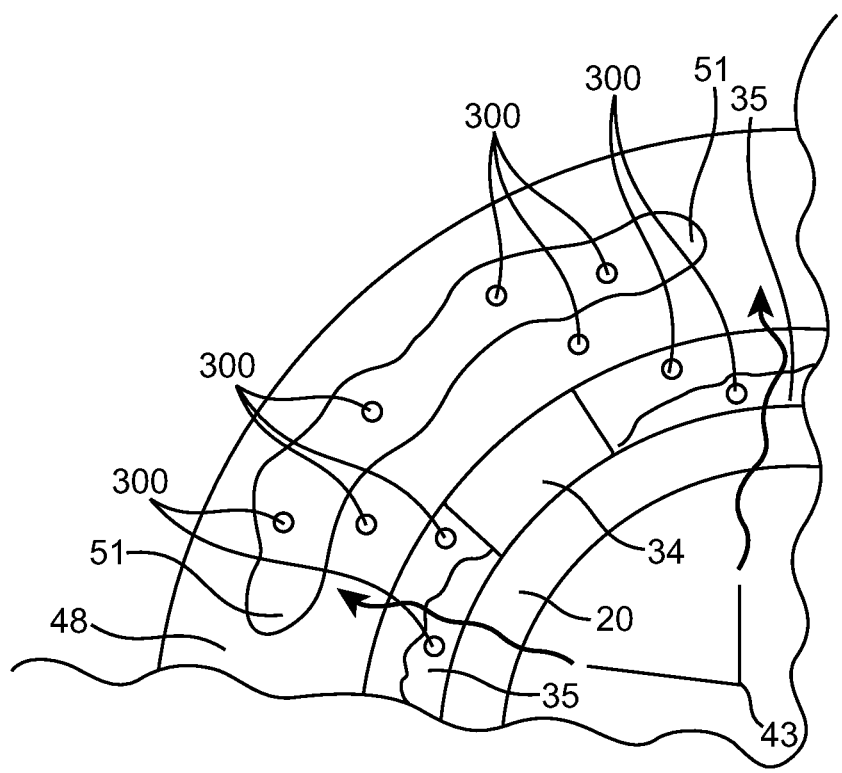
FIG. 12 schematically illustrates release of energy and bioactives from a balloon directed toward a tissue lesion.

By way of example, the release shown in FIG. 10B, FIG. 11C, and FIG. 12, may, at least in part, be caused by coating degradation or dissolution at temperatures above approximately 37 degrees Celsius. Biodegradable Polymers like Polylactic Acid, Polyglycolic Acid, Polyvinyl Acetate, Polyvinyl Propylene, Hydroxypropyl Methylcellulose and Methacrylate polymers can be formulated to degrade more rapidly with increased temperature, thereby releasing bioactive agents more rapidly than if they were held at nominal human body temperature (about 37 degrees Celsius).

By way of another example, the release may at least in part be caused by the liquefying of the coating as it is locally heated above approximately 37 degrees Celsius, wherein the coating may be solid or gel-like at temperatures below approximately 37 degrees Celsius. In yet another example, the coating may break down due to a change in pH such as when the balloon outer surface is placed in contact with a body fluid such as blood. Hydroxypropyl Methylcellulose and Methacrylate polymers are known to rapidly release useful bioactive compounds depending on a change in pH. Galvanic activity triggered by a change in voltage in a localized area may be used to release these compounds in the immediate vicinity of energized electrodes. PEGylated compounds, pNIPA hydrogels, chitosan hydrogels, comb-type graft hydrogels composed of chitosan and poly(N-isopropylacrylamide), and poly(N-isopropylacrylamide) poly(vinyl alcohol) hydrogels, are examples of known hydrogels that may be used as a means for containing and releasing bioactives through a change in temperature, pH, or both.

Most preferably, energy is selectively directed to certain of the electrodes as shown in FIG. 6 by the controller in FIG. 1 and FIG. 7 based on the analysis and selection of diseased tissue targeted for treatment, wherein the electrodes cause localized heating of the balloon coating (FIGS. 5, 9B, 10B, 11C, 12) or outer layer adjacent to the energized electrodes (FIG. 13C) which further causes the release of bioactives from the balloon into the tissue in contact with the energized electrodes. The released dosage of bioactives may be controlled by bioactive concentration levels in the balloon coating or outer layer, and by the quantity of energy directed toward the diseased tissue. The controller shown in FIG. 1 and FIG. 7 may be used to regulate energy applied to the tissue in contact with the electrodes (FIG. 6), to regulate the release of bioactives during heating of the balloon coating or outer layer adjacent to energized electrodes, or a combination thereof. Moreover, it may be further preferable to apply energy to the target tissue such that the uptake of the bioactive into the target tissue is optimized in accordance with the Q10 Rule and within the total energy limits set by the controller.

Shown in FIG. 5, some embodiments of the present invention may include bioactive aptamers coated to the balloon using a substrate that breaks down when heated or exposed to the in vivo environment (FIGS. 3B, 3C, 5, 9B, 10B, 11C, 12, 13C) as described and disclosed. Aptamers are nucleic acids that bind to the surface of molecules in much the same way as antibodies. The term "aptamer" derives from the Latin aptus, "to fit", and was chosen to emphasize the lock-and-key binding relationship between aptamers and their binding partners. Because an extraordinary diversity of molecular shapes exist, aptamers may be obtained for a wide array of molecular targets, which for example, include small molecules, virtually any class of protein, including enzymes, membrane proteins, viral proteins, cytokines and growth factors, immunoglobulins, and even cells, tissues and organisms. For example, aptamers may be synthesized to bind with plaque found in a diseased lumen or artery. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

The balloon coating (such as any of those shown in FIGS. 3B, 3C, 4B, 9A, 10A, 11C, 12) comprised of bioactive aptamers preferably remains intact and attached to the balloon during storage, deployment, and inflation. The bioactive aptamers may be released when a plurality of electrodes is energized. Once released, the bioactive aptamers may bind to the desired tissue, which may then facilitate a biological response. In some embodiments, as shown in FIG. 5, bioactive aptamers may be conjugated to a microscopic bead that preferably is highly receptive to energy emitted by the catheter system, such as RF energy, and the other forms of energy disclosed herein. The conjugated beads may then convert the energy, such as RF energy, to thermal energy allowing for a focused application of bioactives to the selected tissue sites. Additionally, some embodiments may apply energy to the target tissue such that the uptake of the bioactive aptamer into the target tissue is optimized in accordance with the Q10 Rule and within the total energy limits set by the controller. Some embodiments may further comprise coatings such as polymers, gels, lubricant, electrically conductive or non-conductive materials, and the like on surfaces such as the balloon or other surfaces of the catheter system.

As shown in FIG. 11A and FIG. 11C, some embodiments of the present invention may include liposomes 70 (FIG. 11A) coated to the balloon using a substrate that breaks down when heated or exposed to the in vivo environment as described and disclosed herein. For example, liposomes 70 may be incorporated into a polymer or gel matrix (FIG. 11C), or may be directly attached to the outer surface of the balloon. Upon the application of heat, or exposure to the in vivo environment, the liposomes 70 may be activated and released from the outer surface of the balloon (FIG. 11C). As shown in FIG. 11B, liposomes 70 are polar, having one hydrophobic end 74 and one hydrophilic end 73, and are comprised of materials found in cell membranes.

Figure 11D:
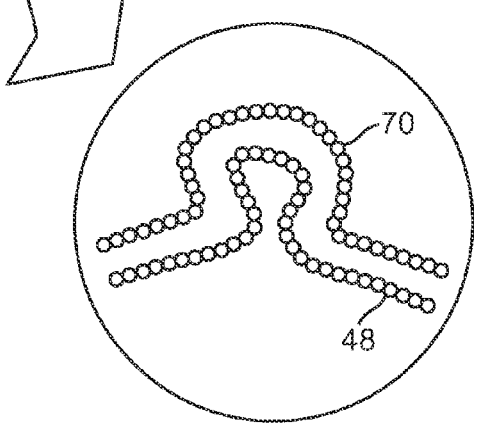
FIG. 11D is an enlarged schematic illustration of tissue uptake of a liposome.

Liposomes, and their related reverse micelles, may contain a core of aqueous solution 72 (FIG. 11A), which may be used to deliver other bioactives to cells because of the ability of liposomes 70 to create pathways through the lipid membrane comprising the cell wall as shown in FIG. 11D. Cell membranes are usually made of phospholipids, which are molecules that have a head group and a tail group. The head is attracted to water (i.e. hydrophilic), and the tail, which is made of a long hydrocarbon chain, is repelled by water (i.e. hydrophobic).

In nature, phospholipids are found in stable membranes composed of two layers (i.e. phospholipid bilayer 71) as shown in FIG. 11B. In the presence of water, the heads are attracted to water and line up to form a surface facing the water. The tails are repelled by water, and line up to form a surface away from the water. In addition to bioactives 50 within the core of the liposome 50c, bioactives may also be attached to the phospholipid heads 50a, phospholipid tails 50b, or any combination thereof (FIG. 11A). In a cell, one layer of heads faces outside of the cell, attracted to the water in the environment. Another layer of heads faces inside the cell, attracted by the water inside the cell. The hydrocarbon tails of one layer face the hydrocarbon tails of the other layer, and the combined structure forms a bilayer.

When membrane phospholipids are disrupted, they can reassemble themselves into tiny spheres, smaller than a normal cell, either as bilayers or monolayers. The bilayer structures are liposomes 70. The monolayer structures are called micelles.

The lipids in the plasma membrane are chiefly phospholipids like phosphatidylethanolamine and phosphatidylcholine. Phospholipids are amphiphilic with the hydrocarbon tail of the molecule being hydrophobic, its polar head hydrophilic. As the plasma membrane faces watery solutions on both sides, its phospholipids accommodate this by forming a phospholipid bilayer with the hydrophobic tails facing each other.

Additionally, some embodiments comprising liposomes may use a plurality of electrodes to apply energy to the target tissue such that the uptake of the bioactive into the target tissue is determined using and/or optimized in accordance with the Q10 Rule and within the total energy limits set by the system controller. Some embodiments may further comprise coatings such as polymers, gels, lubricant, electrically conductive or non-conductive materials, and the like on other surfaces of the catheter system.

In some embodiments, the balloon coating may include a chemical solvent that has plaque softening properties as shown in FIG. 12. By way of example, ether, chloroform, benzene, and acetone are known lipid solvents. Furthermore, amino acids, proteins, carbohydrates, and nucleic acids are largely insoluble in these solvents. If the solvent is used in conjunction with tissue heating (FIG. 6), the tissue treatment may require less energy over a shorter time period, lessening the chance of damage to healthy tissue. If the tissue includes calcium deposits 51, the same process used to deliver lipid solvents to plaque could be used to deliver calcium solvents to calcification sites. Calcium is well known to be highly soluble in a variety of organic solvents. FIG. 12 shows the bioactive including the calcium solvent 300 coated on the balloon 20. In both cases, the solvent may be coupled to the surface of the balloon with a coating that may break down with the application of energy (FIG. 12) as described and disclosed herein, such as heat or RF energy, or the balloon coating may release solvent as the balloon is inflated through coating breakdown, and the like.

In some embodiments, the balloon catheter system (FIGS. 1, 7) may be further comprised to include a means for conducting light energy from a power source, such as the controller, to the balloon portion of the system. The means for conducting light energy may be a fine strand of flexible fiber optic filament placed within a lumen inside of the catheter body. The delivery of light energy may be an alternate or additional source of energy for the release and/or activation of bioactives. For example, an ultraviolet (UV) light source may be used to breakdown a plurality of bioactives on exterior portions of the balloon while simultaneously activating the desired characteristic of the bioactive only after the balloon is positioned at the desired location in vivo. Many advantages of such a light energy means may be envisioned, such advantages include reduced reliance on tissue heating (particularly in prolonged or repetitive treatment situations), the avoidance of transmitting electrical current (such as when working in proximity to a metallic stent implant), preventing the loss of bioactive effect prior to the desired time of release (due to storage or during navigation to the target tissue site), increased variety of bioactives available for delivery, and the like.

In another preferred embodiment of a balloon catheter system, the balloon portion (FIG. 2) is further comprised to include fluid delivery channels, such as those shown in FIG. 8A, for selective delivery of fluids comprised of bioactive material to a body tissue being disposed about a lumen. The catheter system includes a balloon catheter having a catheter body with a proximal end and a distal end such as that shown in FIG. 7. The catheter body is flexible and defines a catheter axis, and may include one or more lumens, such as a guidewire lumen and an inflation lumen (FIG. 7). The catheter includes an inflatable balloon, an adjacent distal end, and a housing adjacent to the proximal end. In some embodiments a housing includes a first connector in communication with a guidewire lumen, and a second connector in fluid communication with the inflation lumen (FIG. 7). The inflation lumen extends between the balloon and the second connector. Both the first and second connectors may optionally comprise a standard connector, such as a LUER-LOC™ connector. Further, a distal tip may include an integral tip valve to allow passage of guidewires, and the like.

The housing may also accommodate an electrical connector, which may preferably include a plurality of electrical connections, each electrically coupled to electrodes (FIG. 8A) via conductors. This arrangement, as shown in FIG. 7, preferably allows the electrodes to be easily energized, the electrodes often being energized by a controller, and power source, such as RF energy, microwave energy, ultrasound energy, or other such suitable energy sources known in the art. In one such embodiment, the electrical connector is coupled to an RF generator via a controller (FIG. 7) that preferably may allow energy to be selectively directed to electrodes (FIGS. 6, 8A). The controller may further include a processor or be coupled to a processor to control or record treatment.

As shown in FIG. 8B, fluid delivery channels pass through the balloon and are preferably coupled to electrodes mounted on the surface of the balloon portion of the balloon catheter system. The electrodes include associated conductors extending proximally from the electrodes. Electrodes and fluid delivery channels may be arranged in many different patterns or arrays on balloon.

In some embodiments, the fluid delivery channels may be coupled to a fluid reservoir or lumen holding the fluid comprised of bioactive material. In some embodiments, the inflation medium may contain the fluid to be delivered (FIGS. 8B, 8C). In some embodiments, the channels through balloon may be filled with materials that liquefy or beak down sufficiently upon heating, such as wax-like materials, gel-like materials, polymers, and the like, whereby the breakdown of the material allows the fluid to pass through the channel upon the application of energy to selected electrodes (FIG. 8B). By way of example, one method includes opening the fluid delivery channels by selectively heating a plurality of the electrodes, through Joule heating or other means, including inducing a heightened temperature in the adjacent region, whereby heat transfer could heat the plurality of selected electrodes such that a material that would otherwise block the channel is phase changed from solid to liquid (FIG. 8B). The energizing of selected electrodes may preferably be based on tissue impedance analysis such as that described herein (FIG. 6). In other embodiments, electromechanical or mechanical means known in the art may be employed to release the fluid, which by way of example may include flaps 165 or microfluidic devices powered by the controller (FIG. 8C).

As shown in FIG. 8C, the delivery channels may protrude from the balloon surface such that they are capable of penetrating body tissue, for example, luminal tissue.

The catheter system may also include a tissue analyzer configured to characterize the body tissue. In some embodiments, electrodes may be sensing electrodes, as those described and disclosed herein, that may aide in the characterization of tissue to identify regions, which may be treated or not, using electrical impedance tomography (FIG. 6). Other characterization means, such as intravascular ultrasound, optical coherence tomography, or the like, may be used to identify regions to be treated. Electrodes may be energized in response to the characterized body tissue.

Some embodiments described herein may be used to treat atherosclerotic disease by selective fluid delivery in combination with the "gentle heating" to further enhance the fluid treatment, as described herein.

In some embodiments, as shown in FIG. 8B and FIG. 8C, the fluid delivery channels may be passages through the electrodes (i.e. perfused electrodes). The passages or small holes may be used to deliver a fluid comprised of bioactive material to the artery tissue proximate the electrode. The passages may be less than 1 µm in diameter and may be made using methods such as a laser or ion beam. The passages may be made in the electrodes and in the balloon. By way of example, electrode pads on a flexible circuit are designed with passages that are plated. The flexible circuit is mounted on a balloon and a laser or ion beam, or other means known in the art, is used to create the passages in the flexible substrate and balloon. There may be several passages in the flexible substrate/balloon for every electrode pad. The balloon may then be perfused with standard perfusion balloon equipment or specialized equipment. The use of perfused electrodes may also provide additional advantages beyond fluid delivery, such as eliminating sticking, carrying away heat, or regulating the impedance of the energized load.

Some embodiments may further comprise coatings such as polymers, gels, lubricant, electrically conductive or non-conductive materials, and the like on surfaces such as the balloon or other surfaces of the catheter system.

Another embodiment for energy induced bioactive material release in a mechanical device is by compaction of the active material with an inert biodegradable. This binary mixture is broken up by exposure to mechanical vibration such as ultrasonic energy when and where needed. The semi solid compaction allows fluid ingress when the vibration breaks surface tension and then is rapidly mixed and dissolved. This liquefaction process may occur over an extended period of time without the energy application, but is greatly enhanced by it.

Figure 13A:
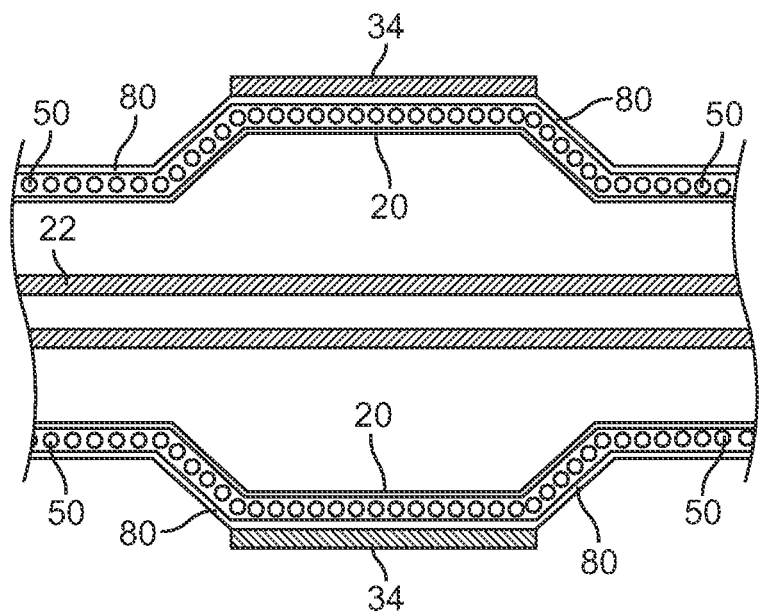
FIG. 13A schematically illustrates another embodiment of a balloon for use in the catheter system of FIG. 1.
Figure 13B:
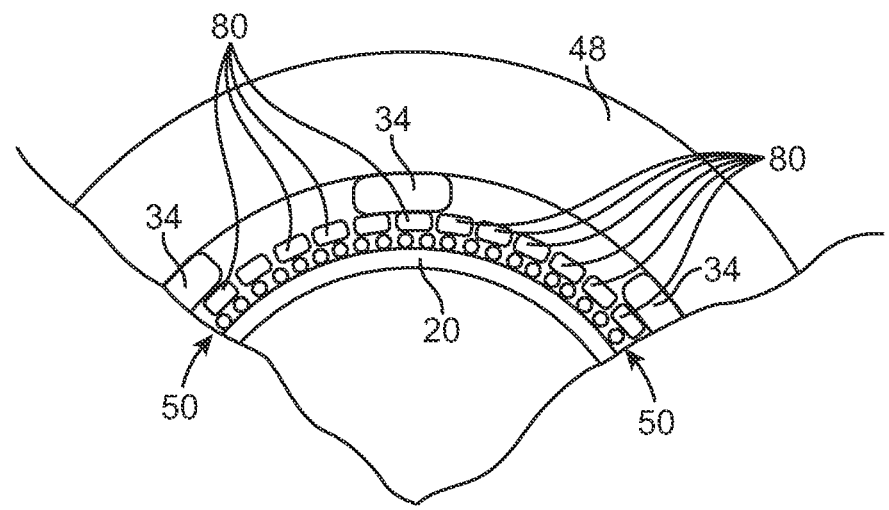
FIG. 13B is an enlarged cross-sectional view of FIG. 13A.

In yet another preferred embodiment of the present invention shown in FIG. 13A, the balloon portion of a balloon catheter is comprised to include a balloon encapsulated by a selectively porous membrane 80 overlaid by a plurality of circumferentially spaced electrodes as shown in FIG. 13B. Most preferably the balloon is comprised of a non-porous, non-compliant material, which may be selected from materials that are well-known in the art. Preferably, a fluid comprised of bioactive material is positioned between the outer surface of the balloon and the inner surface of the selectively porous membrane 80 (FIG. 13B). The balloon may be pressurized to a pressure sufficient to bring it into contact with the inner surface of the luminal tissue, approximately 20 atmospheres or less, most preferably between about 4 atmospheres and about 6 atmospheres of pressure (FIG. 13B).

Figure 13C:
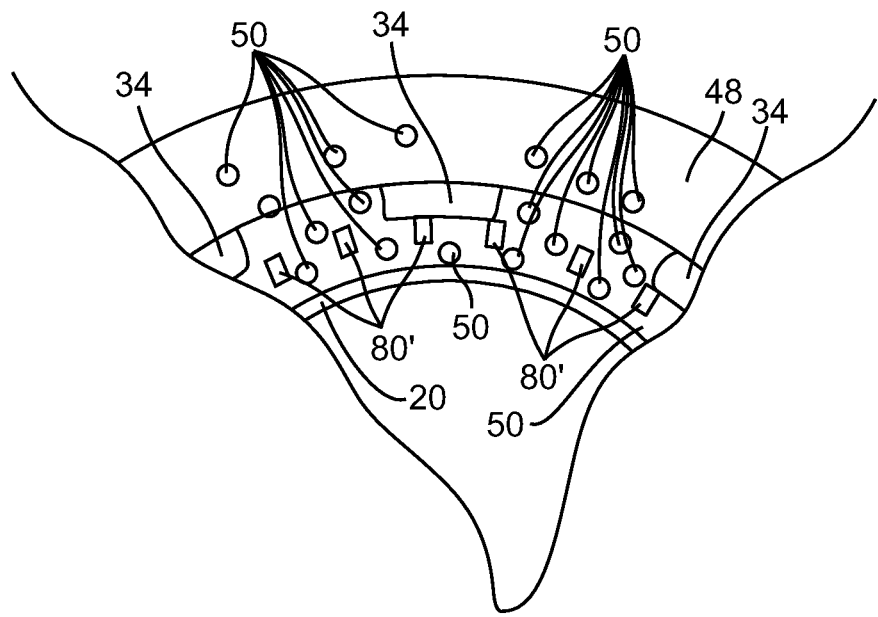
FIG. 13C schematically illustrates the release of bioactives as energy is applied to FIG. 13B.

Most preferably, energy is selectively directed to certain of the electrodes by the controller based on the analysis and selection of diseased tissue targeted for treatment (FIG. 6), wherein the selectively energized electrodes cause localized heating, adjacent to the energized electrodes, of the selectively porous membrane overlaid on the balloon. As shown in FIG. 13C, the localized heating effect on the selectively porous membrane 80', preferably in combination with inflated balloon pressure, may then further allow pores in the membrane to expand to a size that allows the molecules of a fluid comprised of bioactive material to pass through the pores and into targeted tissue, such as that of a diseased arterial lumen. The released dosage of bioactives may be controlled by bioactive concentration levels in the fluid, by the amount of localized membrane heating caused by the energized electrodes, by the inflated pressure of the balloon, by the quantity of energy directed toward the diseased tissue, and by any combination thereof (FIG. 13C). Moreover, it may be further preferable to apply energy to the target tissue such that the uptake of the bioactive into the target tissue is optimized in accordance with the Q10 Rule and within the total energy limits set by the controller. Some embodiments may further comprise coatings such as polymers, gels, lubricant, electrically conductive or non-conductive materials, and the like on surfaces such as the balloon or other surfaces of the catheter system.

Figure 13D:
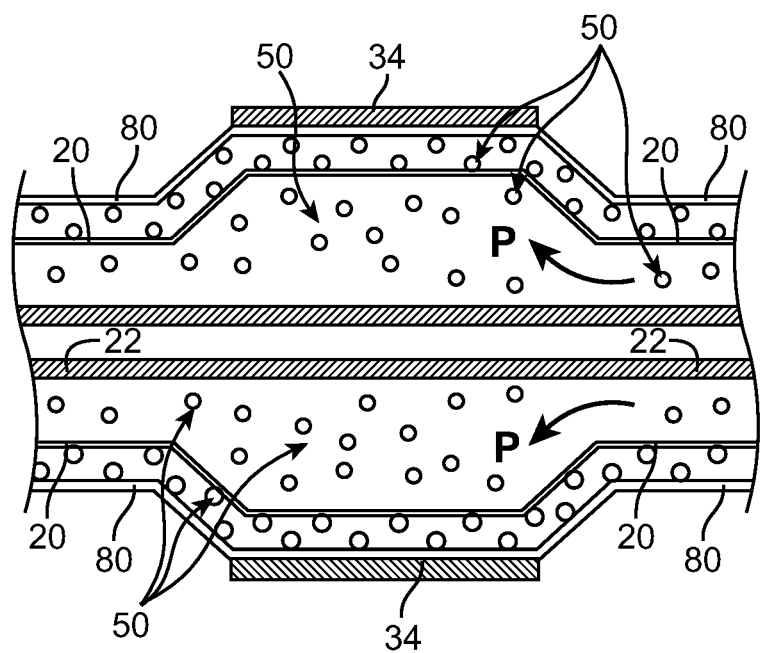
FIG. 13D schematically illustrates another embodiment of FIG. 13A where bioactive comprises an inflation medium for a balloon.

In some alternate embodiments the balloon may be configured such that the inflation media of the balloon is the fluid comprised of bioactive material 50, as shown in FIG. 13D, such that the fluid comprised of bioactive material is introduced between the outer surface of the balloon and the inner surface of the selectively porous membrane 80 upon inflating the balloon to a pressure "P". Fluid communication through the wall of the balloon may be accomplished in any number of ways, which by way of example may include porosity, a plurality of passages, and the like (FIG. 13D). Advantages of such an alternate embodiment include the ability to tailor the concentration and composition of the fluid comprised of bioactives to the nature of the diseased tissue. Moreover, eliminating the storage of perishable bioactives until the therapeutic procedure is performed may extend the shelf life of the balloon catheter. In other alternate embodiments, the balloon may be comprised of any of a variety of known compliant materials, or a combination of balloon compliances to accomplish customized balloon shapes.

Figure 14A:
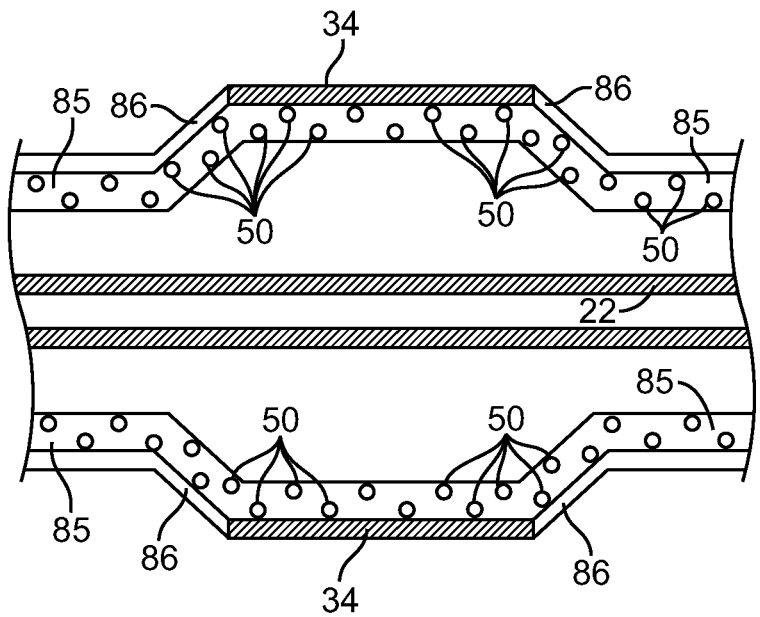
FIG. 14A schematically illustrates yet another embodiment of a balloon for use in the catheter system of FIG. 1.
Figure 14B:
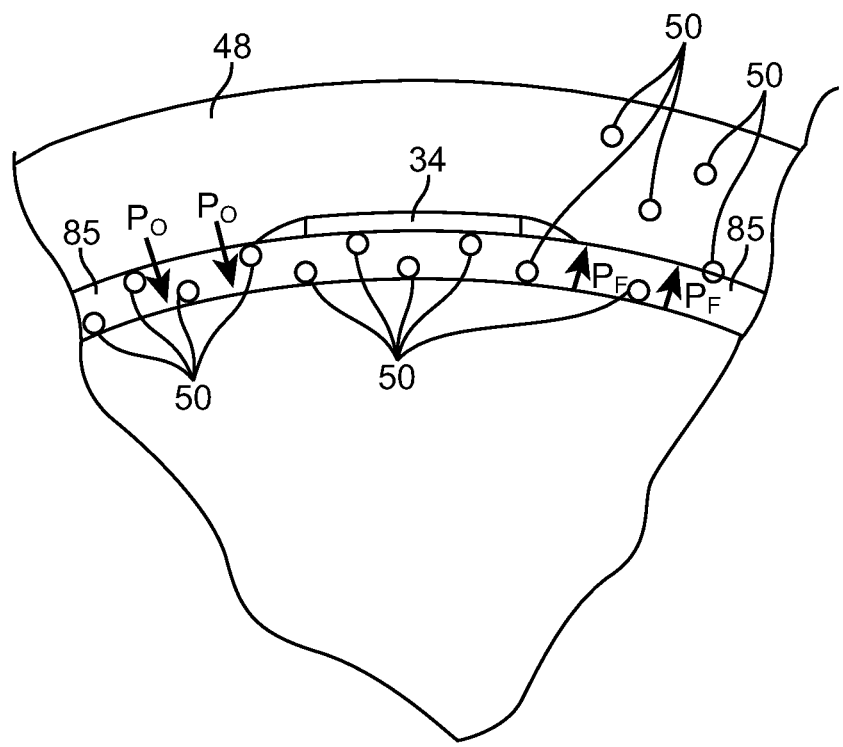
FIG. 14B schematically illustrates the balloon of FIG. 14A releasing bioactives into tissue.

In U.S. Pat. No. 5,383,873, the full disclosure of which is incorporated herein by reference, Hoey, et al. have described the use of osmotic pumping as a means to deliver drugs in vivo. In yet another embodiment shown in FIG. 14A and FIG. 14B, the principles of "osmotic pumping" may be applied to the composition, structure, and use of the bioactive delivery means, such as the balloon embodiments described and disclosed herein. The rate of bioactive delivery is determined by the mechanism of the osmotic release system and is relatively independent of the local micro-environment, such as pH. The delivery means may include a balloon comprised of a biocompatible polymer matrix (FIG. 14A) of the variety known in the art of balloon catheters, or optionally, a flexible matrix overlay may be placed on the exterior surface of the balloon, wherein the overlay is preferably a silicone matrix. A plurality of bioactives 50 may be combined with the biocompatible polymer matrix 85 to comprise the balloon structure (FIGS. 14A, 14B). The balloon structure may be formed using any of the means known in the art. For example, a balloon may be molded and solidified to create a bioactive/polymer matrix 85 construct in the form of the mold in which it hardened. Portions of the balloon may be further covered with an impermeable, biocompatible substance 86, such as polyethylene, such that one may select the region(s), surface, or surfaces from which the release of bioactives may occur (FIG. 14A). When the balloon is applied to a moist surface, such as the tissue of a lumen, fluid enters the interstices of the matrix and solubilizes the bioactive (FIG. 14B). With additional fluid uptake, the bioactive is forced from the matrix as the fluid pressure "$P_f$" overcomes the osmotic pressure "$P_o$" in the bioactive/polymer matrix and diffuses across the thin film of fluid at the balloon/lumen interface. A "pumping" effect is achieved as the fluid pressure is discharged. The osmotic pressure of fluid uptake again takes over until sufficient fluid pressure builds and the "pumping" effect is repeated. The bioactive is carried from the polymer matrix toward the proximate tissue and local concentrations are achieved without significantly affecting systemic concentrations (FIG. 14B). As disclosed and described herein, the balloon may further comprise a plurality electrodes which may be selectively energized to provide additional effect at the tissue treatment site (FIGS. 14A, 14B).

In yet another preferred embodiment of the present invention shown in FIG. 9A, the balloon portion (FIG. 2) of the balloon catheter system may employ the use of bioactive molecules coupled to the balloon in lieu of, or in conjunction with, a coating. The molecules of bioactive may include a thermally releasable active portion and an inert portion coupled by bond, most preferably a covalent bond, to the balloon surface. The active portion or molecule is capable of treating the targeted tissue, which may be enhanced with temperature via selective electrode energizing (FIG. 6), balloon inflation pressure, or a combination thereof. As shown in FIG. 9B, the inert portion of the bioactive molecule stays on the balloon. Most preferably, a balloon catheter system is employed, such as that shown in FIG. 1, wherein low-pressure inflation of the balloon brings a plurality of electrodes circumferentially located about the outer surface of the balloon into contact with diseased tissue such as an atherosclerotic lesion. Electrodes may be selectively energized to target diseased tissue (FIG. 6), as disclosed and described herein, in order to cause hyper-thermal release of the active portion of the bioactive molecule as shown in FIG. 9B. The bioactive molecule is most preferably covalently bound to the balloon, wherein the selective application of energy causes the covalent bond to be broken thereby selectively delivering the active portion of the molecule to the targeted tissue. The bioactive portion of the molecule is released from the portion coupled to the balloon by delivery of energy, such as from a plurality of electrodes (FIGS. 3A, 4A), that induces a localized hyperthermic environment, most preferably above about 37 degrees Celsius. Energy supplied to the electrodes may also include ultrasound-emitting energy.

The most preferable embodiments utilize bioactive molecules that are stable under the hyperthermic conditions. Bioactive molecules may be selected to prevent cell proliferation, cell function, receptor-ligand binding, chemotaxis of inflammatory cells to the target tissue, migration of cells in the native artery strata to the diseased tissue, or any combination thereof. The active portion of the bioactive molecule functions to treat the diseased tissue. By way of example, in an arterial atheroma, bioactives may prevent production of hyperplastic tissue by any means, including, but not limited to, cytostasis (prevention of mitosis), receptor maturation for those receptors at or on cells in the targeted tissue that promote hyperplastic tissue formation.

The influx of the bioactive molecule into the diseased tissue is facilitated and/or hastened by the energy-mediated hyperthermia, i.e., cleavage from the intact bioactive molecule (FIG. 9B), migration into the diseased tissue, and residence in the diseased tissue by virtue of increased porosity.

Additionally, some embodiments may apply energy to the target tissue such that the uptake of the bioactive into the target tissue is optimized in accordance with the Q10 Rule and within the total energy limits set by the controller. Some embodiments may further comprise coatings such as polymers, gels, lubricant, electrically conductive or non-conductive materials, and the like on surfaces such as the balloon or other surfaces of the catheter system.

Selective Delivery of Bioactives to Target Tissue

In some embodiments, an insulating coating such as that shown in FIG. 4A and FIG. 4B, may be used to cover the plurality of electrodes distributed about the surface of the balloon in the balloon catheter system. This coating may be used to insulate the electrodes from the surrounding in vivo environment, and may be comprised of any of the well-known biocompatible materials having insulative properties, and may be applied using any of a broad variety of methods that are well-known, which by way of example may include spray coating parylene over certain of the surfaces of the electrodes or forming a silicone barrier over certain of the surfaces of the electrodes. To illustrate, as shown in FIG. 4C, the insulating coating is preferably used when treating inside or near a metallic object located inside of a lumen, such as a stent where in-stent restenosis is present, because if the electrodes come into contact with metal, they may short circuit and the treatment will end. Therefore, in some embodiments it is preferable for the electrodes to be insulated to avoid short circuit when in proximity with conductive objects such as metals (FIG. 4C), thereby allowing that treatment may continue in such circumstances. The insulating coating may also act to insulate electrodes from tissue, which may cause energy to be directed to selected locations on the balloon while preventing energy from flowing directly to tissue sites. For example, it may be preferable during a palliative treatment of a diseased tissue site to avoid repetitive or prolonged tissue heating while preserving the ability to selectively energize electrodes, create localized balloon heating, and deliver bioactives to a tissue location in a directed manner. The insulating coating may further comprise additional or different bioactives than other regions of the balloon (FIG. 4B). Some embodiments may further comprise additional coatings such as polymers, gels, lubricant, electrically conductive or non-conductive materials, and the like on surfaces such as the balloon or other surfaces of the catheter system.

Directionally Delivered Energy and Bioactives During an Angioplasty Procedure

Some embodiments of the present invention provide systems and methods for delivery of bioactives in a lumen in combination with heating during an angioplasty procedure. Angioplasty is a well-established clinical method for crossing and opening a stenotic lesion (FIG. 4C), wherein stenosis may be partial or complete, diffuse or focal. Various well-known and proven techniques are employed to cross and open a stenotic lesion, inflatable angioplasty balloons comprising an important aspect thereof. Heating the tissue of a lesion may derive additional benefits. For example, heating may cause softening and shrinking of a lesion, which may further enable plaque within the lesion to reshape easily around the balloon, thereby avoiding stretching of the vessel and thus avoiding injury to the vessel. Further additional benefit may be derived by releasing a bioactive during the angioplasty procedure and the heating process. The method for the selective delivery of a bioactive during an angioplasty procedure may be comprised of any of the following steps, which may be further arranged in a variety of orders:

Pressure—due to the balloon in order to open the lumen. The pressure, such as pressure "P" shown in FIG. 13D, may be standard angioplasty dilation pressures of 10-16 atmospheres or may be more gentle dilation pressures of 6 atmospheres or less, and possibly as low as 1 to 2 atmospheres. Balloon pressure may be used incrementally in steps. For example, a balloon may be used as part of the initial process to cross and partially open a highly stenosed lesion, or a balloon may be used to post-dilate a lesion after a stent has been deployed in place after angioplasty. The selective delivery of energy and/or bioactives may be employed at any point during the procedure, or it may be performed at some point after a procedure, such as for treating in-stent restenosis (FIG. 4C), which is a common problem associated with the treatment of vascular disease.

Heating—due to applied energy (FIG. 6) which may soften and shrink the tissue of a lesion. Heating may also have other benefits related to the delivery of bioactives as discussed in relationship to the Q10 Rule, the release of bioactives from the balloon catheter system, and as discussed in many of the embodiments described and disclosed herein.

Bioactives—a plurality of which may be released during the procedure (FIGS. 3B, 3C, 4B, 9B, 10B, 11C, 12, 13C, 14B). Bioactives may be comprised of any material that may produce a biological response. Examples of bioactives may include large or small molecules, and may include, but are not limited to, antiproliferatives, antithrombins, immunosuppressants, lipids, anti-lipids, anti-inflamatories, antineoplastics, antiplatelets, angiogenic agents, anti-angiogentic agents, vitamins, aptamers, antimitotics, metalloproteinase inhibitors, NO donors, estradiols, anti-sclerosing agents, vasoactives, growth factors, beta blockers, AZ blockers, hormones, statins, antioxidants, membrane stabilizing agents, calcium antagonists, retinoid, peptides, lipoproteins, polypeptides, polynucleotides encoding polypeptides, proteins, protein drugs, enzymes, genetic material, cells, energy-activated agents, anti-lymphocytes, and anti-macrophage substances.

Some preferred embodiments include any molecule which will enable prevention or reduction of smooth muscle cell (SMC) proliferation and/or migration from the media to the intima, for example: ceramide, suramin, rapamycin and paclitaxel. The heating of the tissue may have a key role in helping deliver the drug into the lesion or tissue, and deeper into the media.

Other preferred embodiments include proteins such as anti-inflammatory proteins, antibodies and other kinds of proteins which will enable the reduction and healing of the inflammation inside the lesion, or enable prevention or reduction of SMC proliferation and migration. Some embodiments may include proteins that will induce cell apoptosis or oncosis. The heating may have a key role in activating these proteins during the treatment, and if heated quickly during the procedure, enabling the maximum time exposure of the tissue to the proteins. In order to make sure that the proteins will be activated during the procedure, one should take into account the half-life of a protein. The half-life of a protein is the time it takes before any half of the protein pool for that particular protein is still present and functional. The half-life for human proteins depends on many factors but especially environmental factors including temperature. Half-life at very high temperatures (greater than about 50 degrees Celsius) can be in seconds whereas modestly high temperatures (about 42 degrees Celsius to about 45 degrees Celsius) could result in half-life times in the hours range. For a protein-eluting balloon, the proteins are preferably maintained in a storage environment that extends the half-life time. Most preferably, the proteins on the surface of the balloon are stable at temperatures between about 0 degrees Celsius and about 37 degrees Celsius to preserve their bioactive potency until exposed to the in vivo environment and the application of energy. Several of the proteins may be combined to a molecule named Adenosine-5'-triphosphate (ATP). ATP is a multifunctional nucleotide that is important as a "molecular currency" of intracellular energy transfer. In one example, the balloon is covered with the protein and the electrodes are covered with ATP (or the opposite) and the protein will be released with the balloon inflation, and the ATP will be released when the energy will be emitted from the electrodes (or the opposite).

Yet other embodiments may comprise a balloon with cells such as endothelium, or any other type of cell, which may migrate to proximate tissue during the procedure, such as lesion tissue, where the cells may release proteins or antibodies to aide in the healing of inflammation or prevent SMC proliferation and migration. Applied heat may also be used to aide in activating the cells during the procedure.

Yet other embodiments include molecules or proteins that may be attached or become activated when attached to heat shock proteins (HSP). HSP are a group of proteins whose expression is increased when the cells are exposed to elevated temperatures or other stress. For example, HSP27 functions in smooth muscle cells (SMC) migration. The application of RF energy and heating may result in elevation of HSP27 inside the SMC, thereby permitting use of any bioactive, such as a protein, to pass directly to the SMC by using anti-HSP27 antibody. The heat and the outcomes of the heat may facilitate or enhance the use of other molecules or proteins to bind, degrade, inhibit or activate other proteins or cells in the lesion and in the media, in order to prevent restenosis.

In many embodiments, diseased tissue is approached and interrogated using evaluation methods such as tissue impedance measurement (FIG. 6), intravascular ultrasound, optical coherence tomography, or the like, to identify regions to be treated. In an angioplasty procedure, the identification of tissue for treatment may occur at any time before, during, or after the known steps used in angioplasty procedures.

In many embodiments, energy is directed to a plurality of energized electrodes (FIG. 6), which may be further regulated by the use of a controller (FIGS. 1, 7). The development of heat may be used as a method of treatment for diseased tissue, such as that of an arterial lesion where the development of heat is from a location in the balloon catheter system comprising the balloon.

In some embodiments, the energizing of a plurality of electrodes may be used to release bioactives for the treatment of diseased tissue, which for example, may be from a balloon catheter system used for the treatment of vascular disease where such release of bioactives may be from a location in the system comprising the balloon (FIGS. 3B, 3C, 4B, 9B, 10B, 11C, 12, 13C, 14B). The release of bioactives may be at any point during an angioplasty procedure.

In some embodiments, a plurality of electrodes is insulated to prevent the transmission of energy from the balloon catheter system to tissue or conductive objects proximate the balloon portion of the system (FIGS. 4A, 4B, 4C). Such embodiments may be used at any point before, during, or after an angioplasty and/or stenting procedure.

The coatings or layers applied to the balloon (such as any of those shown in FIGS. 3B, 3C, 4B, 9A, 10A, 11C, 12, 14A) and the balloon electrodes (FIGS. 4A, 4C) may be applied using any variety of the established methods used for placing material on or over a surface which may include spraying, dipping, printing, vapor deposition, ionic transfer, and the like.

The devices, systems, and methods disclosed herein may be used to selectively deliver energy and/or bioactives in any artery or location in the vasculature, for example, the femoral, popliteal, coronary and/or carotid arteries. While the disclosure focuses on the use of the technology in the vasculature, the technology would also be useful for any luminal obstruction. Other anatomical structures in which the present invention may be used are the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal. Furthermore, other tissues may be treated by the present invention where less invasive catheter or endoscopic techniques are preferred.

Where reference numbers appear both in the attached figures and in the corresponding figures of Provisional Application No. 61/114,958 and U.S. patent application Ser. No. 12/616,720, those reference numbers generally identify corresponding structures. However, the reference numbers in Table 1 below identify the listed elements.

TABLE 1

| FIG. Number | Reference | Description |
| --- | --- | --- |
| 3C | 35b | Layer of balloon coating |
| | 35c | Another layer of balloon coating |
| 8C | 165 | Flap or "microfluidic device" |
| 10A and B | 50 | Bioactives |
| 11A | 50a | Bioactive attached to head of phospholipid |
| | 50b | Bioactive inside phospholipid bilayer |
| | 50c | Bioactive inside aqueous center of liposome |
| | 70 | Liposome |
| | 71 | Phospholipid bilayer |
| 11B | 73 | Hydrophilic head |
| 11B | 74 | Hydrophilic tail |
| 11C | 43 | Flow of energy toward targeted tissue |
| 11D | | Illustrates liposome combining with membrane of cell in target tissue 48 |
| 12 | 50c | Bioactive including calcium solvent |
| | 51 | Calcific tissue |
| 13A | 80 | Porous membrane |
| 13B | 80 | Porosity shown in detail |

TABLE 1-continued

| FIG. Number | Reference | Description |
|---|---|---|
| 13C | 80' | Expanded porosity after electrode 34 energized |
| 13D | 80 | Passing of bioactive 50 through porous membrane by using pressurization "P" of bioactive 50 as the inflation medium |
| 14A | 85 | Polymer matrix incorporating bioactive 50 |
|  | 86 | Non-permeable coating |
| 14B |  | Illustration of osmotic pumping with osmotic pressure $P_o$ and fluid pressure $P_f$ |
| 14C | 90 | Stent struts with in-stent restenosis |

While the exemplary embodiments have been described in some detail, by way of example and for clarity of understanding, those of skill in the art will recognize that a variety of modifications, adaptations, and changes may be employed. Hence the scope of the present invention should not be limited solely by the appending claims.

What is claimed is:

1. A system for the treatment of a target tissue by directionally delivering energy and/or bioactive material, the system comprising:
   an elongate catheter having a proximal end and a distal end with an axis therebetween, the catheter having a radially expandable balloon near the distal end and an energy delivery surface on the balloon;
   a thermally changeable coating having a releasable bioactive material and coupled to the balloon, the thermally changeable coating being oriented to be urged against the target tissue when the balloon expands;
   wherein the thermally changeable coating has a coating melting temperature greater than 37° C. so that the thermally changeable coating can undergo a phase change to release the bioactive material from the thermally changeable coating; and
   an energy source operatively coupled to the catheter to energize the energy delivery surface so as to heat at least a portion of the thermally changeable coating above the coating melting temperature to melt the portion of the thermally changeable coating and release the bioactive material to the target tissue.

2. The system of claim 1, wherein the energy delivery surface comprises a plurality of spaced electrodes disposed about the expandable balloon, the energy source operatively coupled to the plurality of electrodes so as to selectively energize electrode pairs to heat portions of the thermally changeable coating between the electrode pairs to release the bioactive material to the target tissue.

3. The system of claim 2, wherein the electrodes are coated with an insulating material.

4. The system of claim 1, wherein the balloon is encapsulated by a selectively permeable membrane overlaid by a plurality of circumferentially spaced electrodes.

5. The system of claim 4, wherein the balloon is configured to receive inflation media comprising bioactive material.

6. The system of claim 1, further comprising a tissue analyzer configured to characterize the body tissue.

7. The system of claim 6, wherein the electrode delivery portion is energized to heat the thermally changeable coating to release the bioactive material in response to the characterized body tissue.

8. The system of claim 1, wherein the electrode delivery portion is energized to heat the body tissue before, during and/or after the delivery of the bioactive material.

9. The system of claim 1, wherein the thermally changeable coating includes more than one releasable bioactive material, wherein each material may have a different phase change temperature.

10. The system of claim 1, wherein the bioactive material is selected from at least one of, an antiproliferative, an antithrombin, an immunosuppressant, a lipid, an anti-lipid, a liposome, an anti-inflammatory, an antineoplastic, an antiplatelet, an angiogenic agent, an anti-angiogenic agent, a vitamin, an aptamer, an antimitotic, a metalloproteinase inhibitor, a NO donor, an estradiol, an anti-sclerosing agent, a vasoactive, a growth factor, a beta blocker, an AZ blocker, a hormone, a statin, an antioxidant, a membrane stabilizing agent, a calcium antagonist, a retinoid, a peptide, a lipoprotein, a polypeptide, a polynucleotide encoding polypeptides, a protein, a protein drug, an enzyme, a genetic material, a cell, a chemical solvent, an energy-activated agent, an anti-lymphocyte, an anti-macrophage substance or a combination of any of the above.

11. The system of claim 1, wherein the bioactive material is attached to a portion of a liposome.

12. The system of claim 1, wherein the thermally changeable coating is selected from at least one of, polylactic acid, polyglycolic acid, polyvinyl acetate, polyvinyl propylene, hydroxypropyl methylcellulose, methacrylate or a combination of any of the above.

13. The system of claim 1, wherein the energy source is a RF energy source and the delivery portion is configured to transmit RF energy to release and/or activate at least one bioactive material.

14. The system of claim 1, wherein the energy source is a light energy source and the delivery portion is configured to transmit light energy to release and/or activate at least one bioactive material.

15. A method for the selective delivery of a releasable bioactive material, the method comprising:
   engaging a body tissue disposed about a lumen with a thermally changeable coating by radially expanding a balloon of a catheter, the thermally changeable coating disposed on the balloon;
   wherein the thermally changeable coating has a coating melting temperature greater than 37° C. so that the thermally changeable coating can undergo a phase change to release the bioactive material from the thermally changeable coating;
   energizing a surface on the balloon to heat at least a portion of the thermally changeable coating above the coating melting temperature and at least partially liquefy the thermally changeable coating; and
   releasing the bioactive material from the thermally changeable coating into the body tissue in response to the heating.

16. The method of claim 15, wherein the delivery portion comprises a plurality of electrodes disposed about the expandable balloon and select electrode pairs are energized to heat and liquefy portions of the thermally changeable coating between the electrode pairs.

17. The method of claim 15, wherein the body tissue of the lumen includes a diseased portion and select electrode pairs are energized to heat the thermally changeable coating proximate the diseased portion.

18. The method of claim 15, further comprising characterizing the body tissue to identify body tissue to be treated and selectively heating portions of the thermally changeable coating to release the bioactive material in response to the characterized body tissue to treat the identified body tissue.

19. The method of claim 15, further comprising heating the body tissue before, during and/or after the delivery of the bioactive material.

20. The method of claim 15, wherein the bioactive material is selected from at least one of a therapeutic fluid, an anesthetic drug, a therapeutic drug, a small molecule, a gene therapeutic compound, an anti-thrombolytic agent, a lubricant to allow higher temperatures without sticking, an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

21. The method of claim 15, wherein the delivery portion is energized with RF energy to release and/or activate at least one bioactive material.

22. The method of claim 15, wherein the delivery portion is energized with laser energy to release and/or activate at least one bioactive material.

23. The method of claim 15, wherein the delivery portion is energized with ultrasound energy to release and/or activate at least one bioactive material.

24. The method of claim 15, wherein the delivery portion is energized with microwave energy to release and/or activate at least one bioactive material.

25. A catheter system for bioactive material delivery to a body tissue being disposed about a lumen, the system comprising:
- an elongate catheter having a proximal end and a distal end with an axis therebetween, the catheter having a radially expandable balloon near the distal end and a plurality of electrodes disposed along an outer surface of the balloon for transmission of energy;
- a plurality of biomolecules having a thermally releasable drug portion and an inert portion covalently bound to the balloon; and
- an energy source operatively coupled to a controller to selectively energize the plurality of electrodes so as to heat the biomolecules to release the bioactive material to the body tissue.

\* \* \* \* \*

UNITED STATES PATENT AND TRADEMARK OFFICE
CERTIFICATE OF CORRECTION

PATENT NO.         : 8,551,096 B2                                    Page 1 of 1
APPLICATION NO.    : 12/778037
DATED              : October 8, 2013
INVENTOR(S)        : Mike Perry et al.

It is certified that error appears in the above-identified patent and that said Letters Patent is hereby corrected as shown below:

On the Title Page, Item (73)

Assignee: delete "Boston Scientific Scimed, Inc., Maple Grove, MN (US)" and insert therefor
-- Vessix Vascular, Inc., Laguna Hills, CA (US) --.

Signed and Sealed this
Twenty-second Day of July, 2014

Michelle K. Lee
*Deputy Director of the United States Patent and Trademark Office*